(12) United States Patent
Delcourt et al.

(10) Patent No.: US 9,879,286 B2
(45) Date of Patent: Jan. 30, 2018

(54) METHOD FOR THE ENZYMATIC PRODUCTION OF ISOPRENOL USING MEVALONATE AS A SUBSTRATE

(71) Applicants: Global Bioenergies, Evry (FR); Scientist of Fortune, S.A., Luxembourg (LU)

(72) Inventors: Marc Delcourt, Paris (FR); Maria Anissimova, Nozay (FR); Philippe Marliere, Mouscron (BE)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 0 days.

(21) Appl. No.: 14/390,774

(22) PCT Filed: Apr. 4, 2013

(86) PCT No.: PCT/EP2013/057108
§ 371 (c)(1),
(2) Date: Oct. 4, 2014

(87) PCT Pub. No.: WO2013/150100
PCT Pub. Date: Oct. 10, 2013

(65) Prior Publication Data
US 2015/0118725 A1     Apr. 30, 2015

(30) Foreign Application Priority Data
Apr. 5, 2012  (EP) .................................. 12163330

(51) Int. Cl.
*C12N 1/20*     (2006.01)
*C12P 7/04*     (2006.01)
*C12N 9/88*     (2006.01)
*C12P 5/00*     (2006.01)

(52) U.S. Cl.
CPC .................. *C12P 7/04* (2013.01); *C12N 9/88* (2013.01); *C12P 5/007* (2013.01); *C12Y 401/01033* (2013.01)

(58) Field of Classification Search
None
See application file for complete search history.

(56) References Cited

FOREIGN PATENT DOCUMENTS

WO     2011076261 A1     6/2011

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Guo et al. (H. Guo et al., "Protein Tolerance to Random Amino Acid Change", PNAS 101(25): 9205-9210, Jun. 2004.*
Byres et al, "Crystal Structures of Trypanosoma brucei and *Staphylococcus aureus* Mevalonate Diphosphate Decarboxylase Inform on the Determinants of Specificity and Reactivity", Journal of Molecular Biology, Academic Press, United Kingdom, vol. 371, No. 2, Jul. 13, 2007 (Jul. 13, 2007), pp. 540-553.
International Preliminary Report on Patentabilty in parent PCT application PCT/EP2013/057108.
International Search Report in parent PCT application PCT/EP2013/057108.
Romanowski M J et al, Crystal structure of the *Streptococcus pneumoniae* phosphomevalonate kinase, a member of the GHMP kinase superfamily, Proteins: Structure, Function and Genetics, vol. 47, No. 4, Jun. 1, 2002 (Jun. 1, 2002), pp. 568-571.
Samantha Weerasinghe et al.,"Simulation of structural and functional properties of mevalonate diphosphate decarboxylase (MVD)", Journal of Molecular Modeling, Springer, Verlag , DE, vol. 16, No. 3, Aug. 4, 2009 (Aug. 4, 2009), pp. 489-498.
Written Opinion in parent PCT application PCT/EP2013/057108 dated Jul. 19, 2013.
Written Opinion in parent PCT application PCT/EP2013/057108 dated Mar. 17, 2014.
Office Action dated Jan. 12, 2015 and received in U.S. Appl. No. 13/002,504.
Final Office Action dated Jun. 10, 2015 and received in U.S. Appl. No. 13/002,504.
Office Action dated Sep. 22, 2014 and received in U.S. Appl. No. 13/880,042.
Office Action dated Apr. 22, 2014 and received in U.S. Appl. No. 13/880,042.
Final Office Action dated Aug. 26, 2015 and received in U.S. Appl. No. 13/880,042.
Office Action dated Mar. 14, 2014 and received in U.S. Appl. No. 13/518,146.
Office Action dated Oct. 8, 2014 and received in U.S. Appl. No. 13/518,146.
Restriction Requirement dated Feb. 3, 2015 and received in U.S. Appl. No. 14/367,686.
Office Action dated Jul. 7, and received in U.S. Appl. No. 14/367,686.

\* cited by examiner

*Primary Examiner* — Richard G Hutson
(74) *Attorney, Agent, or Firm* — Michele M. Wales; InHouse Patent Counsel, LLC

(57) ABSTRACT

Described is a method for generating isoprenol through a biological process. More specifically, described is a method for producing isoprenol from mevalonate.

20 Claims, 14 Drawing Sheets

Figure 1:
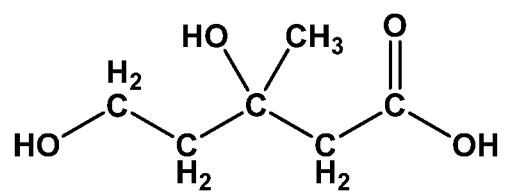

(A) Natural reaction mevalonate 5-diphosphate
(3-hydroxy-3-methyl-5-diphosphopentanoate)

3-phosphonoxy-3-methyl-5-diphosphopentanoate isopentenyl diphosphate (B) Target reaction mevalonate
(3,5-dihydroxy-3-methylpentanoate)

*Phosphorylating step* — ATP → ADP mevalonate 3-phosphate
(3-phosphonoxy-3-methyl-5-hydroxypentanoate)

*Decarboxylating-
dephosphorylating step* → $H_3PO_4$, $CO_2$ isoprenol

Phosphono-phosphate

Phosphonamido--phosphate

SEQUENCE LISTING

<160> NUMBER OF SEQ ID NOS: 22

<210> SEQ ID NO 1
<211> LENGTH: 324
<212> TYPE: PRT
<213> ORGANISM: Picrophilus torridus

```
<400> SEQUENCE: 1

Met Glu Asn Tyr Asn Val Lys Thr Arg Ala Phe Pro Thr Ile Gly Ile
1               5                   10                  15

Ile Leu Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
        35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp
65                  70                  75                  80

Lys Phe Lys His Glu Ile Leu Met Arg Val Asn Leu Asp Asp Glu Asn
                85                  90                  95

Asn Leu Ser Ile Asp Ser Arg Asn Phe Asn Ile Leu Ser Gly Ser Ser
            100                 105                 110

Asp Ser Gly Ala Ala Ala Leu Gly Glu Cys Ile Glu Ser Ile Phe Glu
        115                 120                 125

Tyr Asn Ile Asn Ile Phe Thr Phe Glu Asn Asp Leu Gln Arg Ile Ser
    130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
            180                 185                 190

Ser Asn Glu Ile His Glu Asn Ile Ile Lys His Glu Asn Tyr Arg Glu
        195                 200                 205

Arg Ile Lys Ser Ala Glu Arg Lys Ala Lys Leu Glu Glu Leu Ser
    210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Ile Asn
                245                 250                 255

Asp Arg Met Glu Asn Leu Ile Glu Arg Val Lys Glu Met Lys Asn Asn
            260                 265                 270

Phe Trp Asn Ser Tyr Ile Val Thr Gly Gly Pro Asn Val Phe Val Ile
        275                 280                 285

Thr Glu Lys Lys Asp Val Asp Lys Ala Met Glu Gly Leu Asn Asp Leu
    290                 295                 300

Cys Asp Asp Ile Arg Leu Leu Lys Val Ala Gly Lys Pro Gln Val Ile
305                 310                 315                 320

Ser Lys Asn Phe

<210> SEQ ID NO 2
<211> LENGTH: 318
<212> TYPE: PRT
<213> ORGANISM: Thermoplasma acidophilum

<400> SEQUENCE: 2

Met Thr Tyr Arg Ser Ile Gly Ser Thr Ala Tyr Pro Thr Ile Gly Val
1               5                   10                  15

Val Leu Leu Gly Gly Ile Ala Asn Pro Val Thr Arg Thr Pro Leu His
            20                  25                  30

Thr Ser Ala Gly Ile Ala Tyr Ser Asp Ser Cys Gly Ser Ile Arg Ser
```

```
                35                  40                  45
Glu Thr Arg Ile Tyr Ala Asp Glu Ala Thr His Ile Tyr Phe Asn Gly
     50                  55                  60

Thr Glu Ser Thr Asp Asp Asn Arg Ser Val Arg Val Leu Asp Arg
 65                  70                  75                  80

Tyr Ser Ser Val Phe Glu Glu Ala Phe Gly Thr Lys Thr Val Ser Tyr
                 85                  90                  95

Ser Ser Gln Asn Phe Gly Ile Leu Ser Gly Ser Ser Asp Ala Gly Ala
             100                 105                 110

Ala Ser Ile Gly Ala Ala Ile Leu Gly Leu Lys Pro Asp Leu Asp Pro
             115                 120                 125

His Asp Val Glu Asn Asp Leu Arg Ala Val Ser Glu Ser Ala Gly Arg
             130                 135                 140

Ser Leu Phe Gly Gly Leu Thr Ile Thr Trp Ser Asp Gly Phe His Ala
145                 150                 155                 160

Tyr Thr Glu Lys Ile Leu Asp Pro Glu Ala Phe Ser Gly Tyr Ser Ile
                 165                 170                 175

Val Ala Phe Ala Phe Asp Tyr Gln Arg Asn Pro Ser Asp Val Ile His
             180                 185                 190

Gln Asn Ile Val Arg Ser Asp Leu Tyr Pro Ala Arg Lys Lys His Ala
             195                 200                 205

Asp Glu His Ala His Met Ile Lys Glu Tyr Ala Lys Thr Asn Asp Ile
210                 215                 220

Lys Gly Ile Phe Asp Leu Ala Gln Glu Asp Thr Glu Glu Tyr His Ser
225                 230                 235                 240

Ile Leu Arg Gly Val Gly Val Asn Val Ile Arg Glu Asn Met Gln Lys
                 245                 250                 255

Leu Ile Ser Tyr Leu Lys Leu Ile Arg Lys Asp Tyr Trp Asn Ala Tyr
             260                 265                 270

Ile Val Thr Gly Gly Ser Asn Val Tyr Val Ala Val Glu Ser Glu Asn
             275                 280                 285

Ala Asp Arg Leu Phe Ser Ile Glu Asn Thr Phe Gly Ser Lys Lys Lys
         290                 295                 300

Met Leu Arg Ile Val Gly Gly Ala Trp His Arg Arg Pro Glu
305                 310                 315

<210> SEQ ID NO 3
<211> LENGTH: 320
<212> TYPE: PRT
<213> ORGANISM: Thermoplasma volcanium

<400> SEQUENCE: 3

Met Ser Asn Ser Ser Ile Thr Ser Val Ala Tyr Pro Thr Ile Gly Val
 1               5                  10                  15

Val Leu Leu Gly Gly Ile Ala Asn Glu Lys Thr Arg Thr Pro Leu His
                 20                  25                  30

Thr Ser Ala Gly Ile Ala Tyr Thr Asp Ser Cys Gly Ser Ile Arg Thr
             35                  40                  45

Glu Ser Thr Ile Tyr Gly Asp Ser Glu Met His Ile Tyr Phe Asn Gly
         50                  55                  60

Thr Glu Ser Lys Asp Glu Asn Arg Ser Val Lys Ser Val Leu Glu Arg
 65                  70                  75                  80

Tyr Arg Asn Glu Leu Gln Ser Phe Phe Gly Lys Lys Asp Val Ser Tyr
                 85                  90                  95
```

```
Ser Ser Leu Asn Tyr Gly Ile Leu Ser Gly Ser Ser Asp Ala Gly Ala
            100                 105                 110

Ala Ser Ile Gly Ala Ile Leu Ser Phe Ile Asp Lys Lys Asn Asp Ile
        115                 120                 125

His Asp Ile Glu Asn Asp Ile Arg Met Ile Ser Glu Ser Ala Gly Arg
130                 135                 140

Ser Leu His Gly Gly Leu Thr Ile Thr Trp Ser Asp Gly Tyr Ser Ala
145                 150                 155                 160

Tyr Thr Glu Arg Val Leu Gly Pro Glu His Phe Asn Asn Tyr Ala Ile
                165                 170                 175

Val Gly Phe Ser Phe Asp Tyr Pro Arg Asn Pro Ser Asp Thr Ile His
            180                 185                 190

Gln Asn Ile Ile Lys Ser Lys Arg Tyr Lys Gln Arg Thr Ile Asp Ala
        195                 200                 205

Asp Glu His Ala His Glu Ile Lys Glu Met Ala Arg Thr Asp Asp Ile
210                 215                 220

Glu Gly Ile Phe Glu Lys Ala Glu Glu Asp Thr Glu Glu Tyr His Ser
225                 230                 235                 240

Ile Leu Arg Glu Val Gly Val Leu Val Ile Arg Glu Asn Met Gln Lys
                245                 250                 255

Leu Ile Glu Phe Ile Lys Ile Leu Arg Lys Glu Phe Trp Asn Ser Tyr
            260                 265                 270

Ile Val Thr Gly Gly Ser Asn Val Tyr Val Ile Val Arg Arg Asp Asp
        275                 280                 285

Leu Glu Arg Leu Ile His Ile Lys Asn Thr Phe Gly Ser Lys Pro Lys
290                 295                 300

Ile Leu Asn Val Ala Gly Pro Ala Trp Ile Lys Lys Val Glu Ser Asp
305                 310                 315                 320

<210> SEQ ID NO 4
<211> LENGTH: 322
<212> TYPE: PRT
<213> ORGANISM: Ferroplasma acidarmanus fer1

<400> SEQUENCE: 4

Met Glu Lys Tyr Tyr Val Glu Val Lys Ala Tyr Pro Thr Ile Gly Ile
1               5                   10                  15

Leu Leu Leu Gly Gly Val Ser Asp Asn Lys Lys Arg Leu Pro Arg His
            20                  25                  30

Thr Thr Ala Gly Ile Ala Tyr Thr Gly Leu Asp Asp Asp Ile Tyr Val
        35                  40                  45

Lys Thr Asp Leu Tyr Leu Ser Asn Gln Lys Ser Gly Ile Ile Asn Gly
50                  55                  60

Lys Glu Val Ser Pro Asp Ser Pro Arg Ser Phe Val Val Ile Asp
65                  70                  75                  80

Lys Tyr Arg His Glu Ile Leu Met Arg His Pro Glu Tyr Ser Glu Val
                85                  90                  95

Ser Phe Val Ser Glu Asn Lys Asn Val Ile Ser Gly Ser Ser Asp Ala
            100                 105                 110

Gly Ala Ala Ile Gly Glu Cys Ile Gln Ser Ile Phe Glu Tyr Asn
        115                 120                 125

Ile Asn Ile Phe Asn Phe Glu Asn Asp Leu Gln Gln Ile Ser Glu Ser
130                 135                 140

Ala Gly Arg Ser Met Phe Gly Gly Phe Thr Ile Asn His Ala Asn Gly
145                 150                 155                 160
```

Lys Glu Ser Leu Thr Asp Glu Ile Leu Gly Pro Asp Phe Glu Asp
                165                 170                 175

Phe Val Ile Val Ala Cys Lys Phe Ser Glu Asp Arg Lys Pro Ser Asp
            180                 185                 190

Thr Ile His Ser Asn Ile Ile Asn His Glu Lys Tyr Ala Glu Arg Val
        195                 200                 205

Lys Asn Ser Glu Leu Arg Ala Lys Glu Leu Glu Lys Met Ala Asp Ser
    210                 215                 220

Gly Asp Ile Lys Gly Ile Phe Glu Ala Gly Glu Lys Asp Thr Gln Glu
225                 230                 235                 240

Tyr His Ser Met Leu Arg Glu Val Gly Val Ser Ile Ile Thr Asp Glu
                245                 250                 255

Met Gln Arg Leu Ile Glu Lys Val Glu Glu Leu Lys Ala Glu Phe Trp
            260                 265                 270

Asn Ala Tyr Ile Val Thr Gly Gly Thr Asn Val Phe Val Ala Val Glu
        275                 280                 285

Arg Lys Asn Met Glu Lys Met Lys Asn Ala Ala Met Glu Phe Lys Cys
    290                 295                 300

Thr Pro Val Tyr Leu Lys Val Ala Gly Lys Pro Asp Val Ile Ser Lys
305                 310                 315                 320

Asn Phe

<210> SEQ ID NO 5
<211> LENGTH: 315
<212> TYPE: PRT
<213> ORGANISM: Streptococcus gordonii

<400> SEQUENCE: 5

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Ala Thr Ala Thr Gly Asp Glu Phe Tyr Ile Asp Gly
    50                  55                  60

Gln Leu Gln Ser Pro Ala Glu His Thr Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Ala
        115                 120                 125

Gln Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

```
Asp Tyr Gln Ala Met Leu Ala Tyr Leu Arg Asp Asn Glu Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Ala Ala Ile Leu Glu Lys Asp Tyr Arg Leu Ile
    290                 295                 300

Val Ser Lys Thr Lys Asp Leu Ser Asp Glu Ser
305                 310                 315

<210> SEQ ID NO 6
<211> LENGTH: 315
<212> TYPE: PRT
<213> ORGANISM: Streptococcus gordonii str. Challis substr. CH1

<400> SEQUENCE: 6

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Gly Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Glu Glu Leu Ala Gln Leu Ala Lys Phe Ala Ser Gly Ser Ser Ala Arg
    130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Gln Ala Met Leu Gly Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
```

```
                260                 265                 270
Phe Thr Met Asp Ala Gly Pro Asn Val Lys Val Leu Cys Leu Glu Glu
            275                 280                 285

Asp Leu Asp His Leu Ala Ala Ile Phe Glu Lys Asp Tyr Arg Leu Ile
            290                 295                 300

Val Ser Lys Thr Lys Asp Leu Ser Asp Glu Ser
305                 310                 315

<210> SEQ ID NO 7
<211> LENGTH: 311
<212> TYPE: PRT
<213> ORGANISM: Streptococcus infantarius subsp infantarius ATCC BAA-102

<400> SEQUENCE: 7

Met Asp Arg Lys Ile Val Thr Val Lys Ser Tyr Ala Asn Ile Ala Ile
1               5                   10                  15

Ile Lys Tyr Trp Gly Lys Ala Asp Ala Ala Lys Met Ile Pro Ala Thr
            20                  25                  30

Ser Ser Ile Ser Leu Thr Leu Glu Asn Met Phe Thr Thr Ser Val
        35                  40                  45

Ser Phe Leu Pro Asp Ser Ala Ser His Asp Glu Phe Tyr Ile Asn Gly
    50                  55                  60

Val Leu Gln Asp Asp Lys Glu His Ala Lys Ile Ser Ala Ile Ile Asp
65                  70                  75                  80

Gln Tyr Arg Gly Gln Arg Ser Glu Tyr Val Lys Val Glu Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Thr Arg
        115                 120                 125

Ala Glu Leu Ala Gln Lys Ala Lys Phe Ala Ser Gly Ser Ser Ser Arg
    130                 135                 140

Ser Phe Phe Gly Pro Leu Ala Ala Trp Asp Lys Asp Ser Gly Glu Val
145                 150                 155                 160

Tyr Pro Val Gln Thr Asp Leu Lys Leu Ala Met Ile Met Leu Val Leu
                165                 170                 175

Ser Asp Ser Lys Lys Ser Ile Ser Ser Arg Glu Gly Met Lys Arg Cys
            180                 185                 190

Val Glu Thr Ser Thr Thr Phe Ala Asp Trp Val Lys Gln Ser Glu Gln
        195                 200                 205

Asp Tyr Lys Asp Met Leu Gly Tyr Leu Lys Asn Asn Asp Phe Glu Arg
    210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Glu Glu Ser Tyr Lys
                245                 250                 255

Ala Met Glu Phe Val Lys Gln Leu Arg Ser Glu Gly Glu Lys Cys Tyr
            260                 265                 270

Phe Thr Met Asp Ala Gly Pro Asn Val Lys Val Leu Cys Leu Glu Glu
        275                 280                 285

Asp Leu Glu Arg Leu Thr Lys Arg Phe Glu Glu Asn Tyr Arg Val Ile
    290                 295                 300

Val Ser Arg Thr Lys Glu Leu
305                 310
```

```
<210> SEQ ID NO 8
<211> LENGTH: 391
<212> TYPE: PRT
<213> ORGANISM: Dictyostelium discoideum

<400> SEQUENCE: 8

Met Val Leu Ala Ser Val Thr Cys Thr Ala Pro Val Asn Ile Ala Val
1               5                   10                  15

Ile Lys Tyr Trp Gly Lys Arg Asp Glu Asn Ile Ile Leu Pro Leu Asn
            20                  25                  30

Ser Ser Leu Ser Gly Thr Leu His Gln Asp Asp Leu Lys Thr Thr Thr
        35                  40                  45

Thr Ile Val Ala Ser Glu Asp Tyr Thr Glu Asp Glu Leu Tyr Leu Asn
    50                  55                  60

Gly Lys Lys Glu Asp Ile Asn Ala Val Arg Tyr Gln Asn Val Leu Lys
65                  70                  75                  80

Met Ile Arg Ser Arg Ala Thr Lys Leu Met Asp Lys Lys His Cys Val
                85                  90                  95

His Ile Ala Ser Ile Asn Asn Phe Pro Thr Ala Ala Gly Leu Ala Ser
            100                 105                 110

Ser Ala Ser Gly Tyr Cys Cys Leu Val Phe Thr Leu Ala Gln Met Tyr
        115                 120                 125

Gly Val Asp Gly Asp Ile Ser Gly Ile Ala Arg Leu Gly Ser Gly Ser
    130                 135                 140

Ala Cys Arg Ser Met Tyr Gly Gly Phe Val Lys Trp Glu Met Gly Thr
145                 150                 155                 160

Lys Asp Asp Gly Ser Asp Ser Ile Ala Val Gln Val Gln Pro Glu Ser
                165                 170                 175

His Trp Pro Asp Met Asn Ile Ile Val Leu Val Val Asn Asp Lys Lys
            180                 185                 190

Lys Glu Thr Ser Ser Thr Asp Gly Met Gln Lys Ser Ala Ala Thr Ser
        195                 200                 205

Val Met Met Lys Glu Arg Cys Ala Val Thr Val Pro Asn Arg Met Arg
    210                 215                 220

Asp Ile Glu Glu Ala Ile Asn Lys Lys Asp Phe Gln Thr Phe Gly Asp
225                 230                 235                 240

Ile Thr Met Lys Asp Ser Asp Asp Phe His Glu Val Cys Ala Thr Thr
                245                 250                 255

Thr Pro Pro Ile Tyr Tyr Leu Asn Asp Thr Ser Arg Tyr Ile Met Asn
            260                 265                 270

Leu Ile His Arg Tyr Asn Lys Leu Ser Gly Ser Ile Lys Cys Ala Tyr
        275                 280                 285

Thr Phe Asp Ala Gly Pro Asn Ala Cys Ile Tyr Leu Pro Ala Glu Ser
    290                 295                 300

Thr Thr Glu Val Leu Ser Leu Phe Met Lys His Phe Pro Gly Asp Asp
305                 310                 315                 320

Met Gln Thr Tyr Tyr Arg Gly Pro Lys Glu Asn Ile Pro Ser Ile Glu
                325                 330                 335

Asn Phe Val Pro Ser Glu Lys Leu Ala Ser Leu Tyr Thr Pro Asp Thr
            340                 345                 350

Thr Phe Val Asn Ser Leu Lys Tyr Ile Leu His Thr Lys Val Gly Pro
        355                 360                 365

Gly Pro Gln Ile Leu Ser Glu Ser Glu Ser Leu Ile Asp Asn Thr Thr
    370                 375                 380
```

```
Gly Leu Pro Lys Gln Leu Asn
385                 390

<210> SEQ ID NO 9
<211> LENGTH: 319
<212> TYPE: PRT
<213> ORGANISM: Lactobacillus delbrueckii

<400> SEQUENCE: 9

Met Ser Lys Thr Ala Arg Ala His Thr Asn Ile Ala Leu Ile Lys Tyr
1               5                   10                  15

Trp Gly Lys Lys Asp Ala Lys Leu Arg Leu Pro Leu Met Ser Ser Leu
            20                  25                  30

Ser Met Thr Leu Asp Ala Phe Tyr Ser Asp Thr Lys Ile Ser Asp Ser
        35                  40                  45

Glu Gln Met Ser Phe Lys Leu Asn Gly Gln Ala Val Ser Gly Pro Ala
    50                  55                  60

Ala Asp Arg Val Phe Ala Tyr Leu Arg Ala Met Gln Asp Arg Phe Gly
65                  70                  75                  80

Val Lys Gly Asn Leu Ala Val Glu Ser Val Asn Gln Val Pro Thr Ala
                85                  90                  95

Ala Gly Leu Ala Ser Ser Ser Ala Phe Ala Met Ala Ala Ala
            100                 105                 110

Phe Ala Asp His Tyr Gln Leu Gly Val Asp Arg Gln Glu Leu Ser Arg
            115                 120                 125

Met Ala Arg Met Gly Ser Gly Ser Ala Ser Arg Ser Val Phe Gly Gly
    130                 135                 140

Phe Ser Val Trp Gln Lys Gly Asp Ser Asp Gln Thr Ser Tyr Ala Tyr
145                 150                 155                 160

Pro Leu Asp Glu Glu Pro Asp Met Asp Leu Arg Leu Leu Ala Val Glu
                165                 170                 175

Ile Asn Asp Gln Glu Lys Lys Ile Ser Ser Thr Lys Gly Met Glu Met
            180                 185                 190

Ser Lys Ser Ser Pro Phe Tyr Gln Val Trp Leu Asp Arg Asn Asp Ser
        195                 200                 205

Glu Ile Lys Glu Met Glu Ala Ile Lys Gln Ala Asp Phe Ser Lys
    210                 215                 220

Leu Gly Ser Leu Ala Glu Leu Asn Ala Ser Glu Met His Thr Leu Thr
225                 230                 235                 240

Phe Thr Ala Val Pro Gly Phe Thr Tyr Phe Glu Pro Asn Thr Ile Lys
                245                 250                 255

Ala Ile Lys Leu Val Gln Asp Leu Arg Gln Gln Gly Leu Glu Cys Tyr
            260                 265                 270

Tyr Thr Ile Asp Ala Gly Pro Asn Val Lys Val Leu Cys Gln Gly Lys
        275                 280                 285

Asn Ser Lys Asp Ile Ile Asn Cys Phe Glu Ser Ser Phe Asp Arg Val
    290                 295                 300

Lys Ile Ile Glu Ala Gly Phe Gly Pro Gly Val Thr Leu Leu Asp
305                 310                 315

<210> SEQ ID NO 10
<211> LENGTH: 317
<212> TYPE: PRT
<213> ORGANISM: Streptococcus mitis (strain B6)

<400> SEQUENCE: 10
```

```
Met Asp Arg Glu Pro Val Thr Val Arg Ser Tyr Ala Asn Ile Ala Ile
1               5                   10                  15

Ile Lys Tyr Trp Gly Lys Lys Glu Lys Met Val Pro Ala Thr
            20                  25                  30

Ser Ser Ile Ser Leu Thr Leu Glu Asn Met Tyr Thr Glu Thr Thr Leu
        35                  40                  45

Ser Ser Leu Pro Thr Asp Ala Thr Ala Asp Ala Phe Tyr Ile Asn Gly
    50                  55                  60

Gln Leu Gln Asn Glu Ala Glu His Val Lys Met Ser Lys Ile Ile Asp
65                  70                  75                  80

Arg Tyr Arg Pro Asp Gly Asp Gly Phe Val Arg Ile Asp Thr Gln Asn
                85                  90                  95

Ser Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Gly Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Val Tyr Leu Lys Ala Asn Asp Phe Ala Lys
    210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ala Cys Tyr
            260                 265                 270

Phe Thr Met Asp Ala Gly Pro Asn Val Lys Val Leu Cys Gln Glu Lys
        275                 280                 285

Asp Leu Glu His Leu Ser Glu Ile Phe Gly Gln Arg Tyr Arg Leu Ile
    290                 295                 300

Val Ser Lys Thr Lys Asp Leu Ser Gln Asp Gly Cys Cys
305                 310                 315

<210> SEQ ID NO 11
<211> LENGTH: 316
<212> TYPE: PRT
<213> ORGANISM: Streptococcus gallolyticus UCN34

<400> SEQUENCE: 11

Met Asp Arg Lys Ile Val Thr Val Lys Ser Tyr Ala Asn Ile Ala Ile
1               5                   10                  15

Ile Lys Tyr Trp Gly Lys Ala Asp Ala Val Lys Met Ile Pro Ala Thr
            20                  25                  30

Ser Ser Ile Ser Leu Thr Leu Glu Asn Met Phe Thr Thr Thr Val
        35                  40                  45

Ser Phe Leu Pro Gln Ser Val Gly His Asp Glu Phe Tyr Ile Asn Gly
```

```
            50                  55                  60
Val Leu Gln Asp Glu Lys Glu His Ala Lys Ile Ser Ala Ile Ile Asp
 65                  70                  75                  80

Gln Tyr Arg Gly Gly Arg Ser Glu Phe Val Lys Val Glu Thr Ser Asn
                 85                  90                  95

Asn Met Pro Thr Ala Ala Gly Leu Ser Ser Ser Ser Gly Leu Ser
            100                 105                 110

Ala Leu Val Lys Ala Cys Asn Glu Leu Phe Glu Thr Gly Leu Asn Gln
                115                 120                 125

Ser Glu Leu Ala Gln Lys Ala Lys Phe Ala Ser Gly Ser Ser Ser Arg
            130                 135                 140

Ser Phe Phe Gly Pro Ile Ala Ala Trp Asp Lys Asp Ser Gly Asp Ile
145                 150                 155                 160

Tyr Pro Val Gln Thr Asp Leu Lys Leu Ala Met Ile Met Leu Val Leu
                165                 170                 175

Ser Asp Ser Lys Lys Pro Ile Ser Ser Arg Glu Gly Met Lys Arg Cys
            180                 185                 190

Ala Glu Thr Ser Thr Thr Phe Ala Asp Trp Val Lys Gln Ser Glu Gln
                195                 200                 205

Asp Tyr Lys Asp Met Leu Ala Tyr Leu Lys Ala Asn Asp Phe Glu Lys
            210                 215                 220

Val Gly Glu Leu Thr Glu Arg Asn Ala Leu Ala Met His Asp Thr Asn
225                 230                 235                 240

Thr His Ala Asn Pro Pro Phe Asn Tyr Leu Thr Asp Glu Thr Tyr Ala
                245                 250                 255

Ala Met Asp Phe Val Lys Ser Leu Arg Thr Gln Gly Glu Lys Cys Tyr
            260                 265                 270

Phe Thr Met Asp Ala Gly Pro Asn Val Lys Val Leu Cys Leu Glu Glu
            275                 280                 285

Asp Leu Glu Cys Leu Thr Lys Arg Phe Glu Asn Tyr Arg Val Ile
            290                 295                 300

Ala Ser Arg Thr Lys Val Leu Pro Asp Glu Asn Asp
305                 310                 315

<210> SEQ ID NO 12
<211> LENGTH: 315
<212> TYPE: PRT
<213> ORGANISM: Streptococcus sanguinis SK36

<400> SEQUENCE: 12

Met Asp Arg Lys Pro Val Ser Val Lys Ser Tyr Ala Asn Ile Ala Ile
  1               5                  10                  15

Val Lys Tyr Trp Gly Lys Lys Asp Ala Glu Lys Met Ile Pro Ser Thr
                 20                  25                  30

Ser Ser Ile Ser Leu Thr Leu Glu Asn Met Tyr Thr Glu Thr Gln Leu
             35                  40                  45

Ser Pro Leu Pro Asp Thr Ala Thr Gly Asp Glu Phe Tyr Ile Asp Ser
         50                  55                  60

Gln Leu Gln Ser Pro Ala Glu His Ala Lys Ile Ser Lys Ile Ile Asp
 65                  70                  75                  80

Arg Phe Arg Ser Pro Glu Asp Gly Phe Val Arg Val Asp Thr Ser Asn
                 85                  90                  95

Asn Met Pro Thr Ala Ala Gly Leu Ser Ser Ser Ser Gly Leu Ser
            100                 105                 110
```

```
Ala Leu Val Lys Ala Cys Asn Ala Tyr Phe Gln Thr Gly Tyr Gln Thr
            115                 120                 125

Gln Glu Leu Ala Gln Leu Ala Lys Phe Ala Ser Gly Ser Ser Ala Arg
        130                 135                 140

Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
                165                 170                 175

His Asp Glu Lys Lys Pro Ile Ser Ser Arg Asp Gly Met Glu Leu Cys
            180                 185                 190

Ala Lys Thr Ser Thr Ile Phe Pro Asp Trp Ile Ala Gln Ser Ala Leu
        195                 200                 205

Asp Tyr Lys Ala Met Leu Ser Tyr Leu Gln Asp Asn Asp Phe Ala Lys
    210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
                245                 250                 255

Ala Met Asp Ala Val Arg Lys Leu Arg Glu Gln Gly Glu Arg Cys Tyr
            260                 265                 270

Phe Thr Met Asp Ala Gly Pro Asn Val Lys Val Leu Cys Leu Glu Glu
        275                 280                 285

Asp Leu Asp His Leu Val Ala Ile Phe Glu Lys Asp Tyr Arg Leu Ile
    290                 295                 300

Val Ser Lys Thr Lys Asp Leu Ser Asp Glu Asp
305                 310                 315

<210> SEQ ID NO 13
<211> LENGTH: 317
<212> TYPE: PRT
<213> ORGANISM: Streptococcus sp. M143

<400> SEQUENCE: 13

Met Asp Arg Lys Pro Val Thr Val Arg Ser Tyr Ala Asn Ile Ala Ile
1               5                   10                  15

Ile Lys Tyr Trp Gly Lys Lys Lys Glu Lys Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Thr Asp Ala Thr Ala Asp Ala Phe Tyr Ile Asn Gly
50                  55                  60

Gln Leu Gln Ser Glu Ala Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Leu Gly Leu Asn Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175
```

```
Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Leu Tyr Leu Lys Glu Asn Asp Phe Ala Lys
210                 215                 220

Val Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
                245                 250                 255

Ala Met Asp Phe Val Arg Gln Leu Arg Glu Gln Gly Glu Ser Cys Tyr
            260                 265                 270

Phe Thr Met Asp Ala Gly Pro Asn Val Lys Val Leu Cys Gln Glu Glu
            275                 280                 285

Asp Leu Glu His Leu Ser Glu Ile Phe Gly Arg Tyr Arg Leu Ile
290                 295                 300

Val Ser Lys Thr Lys Asp Leu Ser Gln Asp Asp Cys Cys
305                 310                 315

<210> SEQ ID NO 14
<211> LENGTH: 341
<212> TYPE: PRT
<213> ORGANISM: Streptococcus suis 89/1591

<400> SEQUENCE: 14

Met Thr Lys Gln Ile Gly Ile Ala Arg Ala His Thr Asn Ile Ala Leu
1               5                   10                  15

Ile Lys Tyr Trp Gly Lys Arg Asp Lys Glu Leu Phe Leu Pro Met Asn
            20                  25                  30

Ser Ser Leu Ser Leu Thr Leu Asp Ala Phe Tyr Thr Asp Thr Lys Val
        35                  40                  45

Val Phe Asp Pro Glu Leu Thr Ala Asp Glu Phe Tyr Leu Asn Gly Met
    50                  55                  60

Leu Gln Lys Glu Lys Glu Ile Leu Lys Ile Ser Arg Phe Leu Asp Leu
65                  70                  75                  80

Phe Cys Glu Tyr Ile Gly Glu Arg Ala Phe Ala Arg Val Glu Ser Leu
                85                  90                  95

Asn Phe Val Pro Thr Ala Ala Gly Leu Ala Ser Ser Ala Ser Ala Phe
            100                 105                 110

Ala Ala Leu Ala Leu Ala Thr Ala Thr Ala Leu Asp Leu Asp Leu Ser
        115                 120                 125

Pro Ala Thr Leu Ser Thr Leu Ala Arg Arg Gly Ser Gly Ser Ser Thr
    130                 135                 140

Arg Ser Leu Phe Gly Gly Phe Val Glu Trp Asp Met Gly Thr Gly Ser
145                 150                 155                 160

Glu Asp Ser Met Ala His Pro Ile Asp Asp Ala Asp Trp Asp Ile Gly
                165                 170                 175

Met Val Val Leu Ala Val Asn Thr Gly Pro Lys Lys Ile Ala Ser Arg
            180                 185                 190

Glu Gly Met Asp His Thr Val Ala Thr Ser Pro Phe Tyr Ser Ala Trp
        195                 200                 205

Val Asp Thr Ala Lys Gln Asp Leu Ala Asp Ile Lys Ala Ala Ile Ala
    210                 215                 220

Gly Arg Asp Phe Glu Lys Leu Gly Gln Ile Thr Glu His Asn Gly Met
```

```
                    225                 230                 235                 240

Lys Met His Ala Thr Thr Leu Ser Ala Asn Pro Pro Phe Thr Tyr Trp
                245                 250                 255

Ser Ala Asp Ser Leu Val Ala Gln Glu Ala Val Arg Gln Val Arg Glu
                260                 265                 270

Ala Thr Gly Leu Ser Ala Tyr Met Thr Met Asp Ala Gly Pro Asn Val
                275                 280                 285

Lys Val Leu Cys Arg Ala Ser Gln Met Asp Glu Leu Val Ala Glu Leu
                290                 295                 300

Ala Lys Val Phe Pro Arg Glu Lys Ile Ile Thr Ser Lys Pro Gly Pro
305                 310                 315                 320

Ala Ala Tyr Val Leu Ser Glu Asp Glu Trp Gln Thr Ser Gln Ala Ala
                325                 330                 335

Phe Glu Lys Gly Leu
                340

<210> SEQ ID NO 15
<211> LENGTH: 314
<212> TYPE: PRT
<213> ORGANISM: Streptococcus salivarius SK126

<400> SEQUENCE: 15

Met Asp Arg Lys Pro Val Ser Val Lys Ser Tyr Ala Asn Ile Ala Ile
1               5                   10                  15

Val Lys Tyr Trp Gly Lys Ala Asp Ala Glu Arg Met Ile Pro Ser Thr
                20                  25                  30

Ser Ser Ile Ser Leu Thr Leu Glu Asn Met Tyr Thr Glu Thr Lys Leu
                35                  40                  45

Ser Phe Leu Pro Glu Asp Ala Thr Gly Asp Val Met Tyr Ile Asp Asp
                50                  55                  60

Glu Leu Gln Gly Glu Lys Glu Thr Thr Lys Ala Ser Lys Val Leu Asp
65                  70                  75                  80

Leu Phe Arg Asn Asn Ser Asn Gln His Val Lys Ile Glu Thr Trp Asn
                85                  90                  95

Asn Met Pro Thr Ala Ala Gly Leu Ser Ser Ser Ser Ser Gly Leu Ser
                100                 105                 110

Ala Leu Val Lys Ala Ala Asn Glu Leu Phe Gln Val Gly Lys Thr Gln
                115                 120                 125

Ser Glu Leu Ala Gln Ile Ala Lys Phe Ala Ser Gly Ser Ser Ser Arg
                130                 135                 140

Ser Phe Phe Gly Pro Leu Ala Ala Trp Asp Lys Asp Ser Gly Glu Val
145                 150                 155                 160

Tyr Pro Val Glu Thr Asp Leu Lys Leu Ala Met Ile Met Leu Val Leu
                165                 170                 175

Thr Asp Gln Lys Lys Pro Val Ser Ser Arg Asp Gly Met Lys Leu Cys
                180                 185                 190

Thr Glu Thr Ser Thr Ser Phe Pro Glu Trp Ile Lys Gln Ser Glu Leu
                195                 200                 205

Asp Tyr Lys Asp Met Leu Ala Tyr Leu Lys Ala Asn Asp Phe Gln Ala
                210                 215                 220

Val Gly Glu Leu Thr Glu Ala Asn Ala Leu Arg Met His Gln Thr Thr
225                 230                 235                 240

Ser Thr Ala Asn Pro Pro Phe Ser Tyr Leu Thr Glu Ala Ser Tyr Gln
                245                 250                 255
```

```
Ala Met Asp Lys Val Lys Ala Leu Arg Ala Ser Gly Glu Gln Cys Tyr
            260                 265                 270

Phe Thr Met Asp Ala Gly Pro Asn Val Lys Val Leu Cys Leu Glu Glu
        275                 280                 285

Asp Leu Asp Arg Leu Ala Glu His Phe Arg Lys Asp Tyr Gln Val Ile
    290                 295                 300

Val Ser Arg Thr Lys Glu Leu Pro Asp Ala
305                 310

<210> SEQ ID NO 16
<211> LENGTH: 325
<212> TYPE: PRT
<213> ORGANISM: Thermoplasma acidophilum

<400> SEQUENCE: 16

Met Leu His His His His His His Thr Tyr Arg Ser Ile Gly Ser Thr
1               5                   10                  15

Ala Tyr Pro Thr Ile Gly Val Val Leu Leu Gly Gly Ile Ala Asn Pro
            20                  25                  30

Val Thr Arg Thr Pro Leu His Thr Ser Ala Gly Ile Ala Tyr Ser Asp
        35                  40                  45

Ser Cys Gly Ser Ile Arg Ser Glu Thr Arg Ile Tyr Ala Asp Glu Ala
    50                  55                  60

Thr His Ile Tyr Phe Asn Gly Thr Glu Ser Thr Asp Asp Asn Arg Ser
65                  70                  75                  80

Val Arg Arg Val Leu Asp Arg Tyr Ser Ser Val Phe Glu Glu Ala Phe
                85                  90                  95

Gly Thr Lys Thr Val Ser Tyr Ser Ser Gln Asn Phe Gly Ile Leu Ser
            100                 105                 110

Gly Ser Ser Asp Ala Gly Ala Ala Ser Ile Gly Ala Ala Ile Leu Gly
        115                 120                 125

Leu Lys Pro Asp Leu Asp Pro His Asp Val Glu Asn Asp Leu Arg Ala
    130                 135                 140

Val Ser Glu Ser Ala Gly Arg Ser Leu Phe Gly Gly Leu Thr Ile Thr
145                 150                 155                 160

Trp Ser Asp Gly Phe His Ala Tyr Thr Glu Lys Ile Leu Asp Pro Glu
                165                 170                 175

Ala Phe Ser Gly Tyr Ser Ile Val Ala Phe Ala Phe Asp Tyr Gln Arg
            180                 185                 190

Asn Pro Ser Asp Val Ile His Gln Asn Ile Val Arg Ser Asp Leu Tyr
        195                 200                 205

Pro Ala Arg Lys Lys His Ala Asp Glu His Ala His Met Ile Lys Glu
    210                 215                 220

Tyr Ala Lys Thr Asn Asp Ile Lys Gly Ile Phe Asp Leu Ala Gln Glu
225                 230                 235                 240

Asp Thr Glu Glu Tyr His Ser Ile Leu Arg Gly Val Gly Val Asn Val
                245                 250                 255

Ile Arg Glu Asn Met Gln Lys Leu Ile Ser Tyr Leu Lys Leu Ile Arg
            260                 265                 270

Lys Asp Tyr Trp Asn Ala Tyr Ile Val Thr Gly Gly Ser Asn Val Tyr
        275                 280                 285

Val Ala Val Glu Ser Glu Asn Ala Asp Arg Leu Phe Ser Ile Glu Asn
    290                 295                 300

Thr Phe Gly Ser Lys Lys Lys Met Leu Arg Ile Val Gly Gly Ala Trp
305                 310                 315                 320
```

His Arg Arg Pro Glu
            325

<210> SEQ ID NO 17
<211> LENGTH: 267
<212> TYPE: PRT
<213> ORGANISM: Methanosarcina mazei

<400> SEQUENCE: 17

Met Glu Met Arg Gln Pro Ala Val Ala Gly Gln Phe Tyr Pro Leu Arg
1               5                   10                  15

Cys Glu Asn Leu Glu Asn Glu Leu Lys Arg Cys Phe Glu Gly Leu Glu
            20                  25                  30

Ile Arg Glu Gln Glu Val Leu Gly Ala Val Cys Pro His Ala Gly Tyr
        35                  40                  45

Met Tyr Ser Gly Lys Val Ala Ala His Val Tyr Ala Thr Leu Pro Glu
    50                  55                  60

Ala Asp Thr Tyr Val Ile Phe Gly Pro Asn His Thr Gly Tyr Gly Ser
65                  70                  75                  80

Pro Val Ser Val Ser Arg Glu Thr Trp Lys Thr Pro Leu Gly Asn Ile
                85                  90                  95

Asp Val Asp Leu Glu Leu Ala Asp Gly Phe Leu Gly Ser Ile Val Asp
            100                 105                 110

Ala Asp Glu Leu Gly His Lys Tyr Glu His Ser Ile Glu Val Gln Leu
        115                 120                 125

Pro Phe Leu Gln Tyr Arg Phe Glu Arg Asp Phe Lys Ile Leu Pro Ile
    130                 135                 140

Cys Met Gly Met Gln Asp Glu Glu Thr Ala Val Glu Val Gly Asn Leu
145                 150                 155                 160

Leu Ala Asp Leu Ile Ser Glu Ser Gly Lys Arg Ala Val Ile Ile Ala
                165                 170                 175

Ser Ser Asp Phe Thr His Tyr Glu Thr Ala Glu Arg Ala Lys Glu Ile
            180                 185                 190

Asp Ser Glu Val Ile Asp Ser Ile Leu Asn Phe Asp Ile Ser Gly Met
        195                 200                 205

Tyr Asp Arg Leu Tyr Arg Arg Asn Ala Ser Val Cys Gly Tyr Gly Pro
    210                 215                 220

Ile Thr Ala Met Leu Thr Ala Ser Lys Lys Leu Gly Gly Ser Arg Ala
225                 230                 235                 240

Thr Leu Leu Lys Tyr Ala Asn Ser Gly Asp Val Ser Gly Asp Lys Asp
                245                 250                 255

Ala Val Val Gly Tyr Ala Ala Ile Ile Val Glu
            260                 265

<210> SEQ ID NO 18
<211> LENGTH: 326
<212> TYPE: PRT
<213> ORGANISM: Sulfolobus tokodaii

<400> SEQUENCE: 18

Met Arg Leu Glu Ala Glu Ala Ile Ala Pro Ser Asn Ile Ala Ile Ile
1               5                   10                  15

Lys Tyr Trp Gly Lys Arg Asn Glu Glu Leu Asn Leu Pro Leu Asn Ser
            20                  25                  30

Ser Leu Ser Val Thr Leu Ser Gly Leu Glu Val Lys Thr Lys Ile Thr
        35                  40                  45

-continued

```
Phe Ser Lys Glu Phe Thr Lys Asp Glu Val Tyr Ile Asn Gly Glu Arg
         50                  55                  60

Ala Lys Asp Glu Glu Val Lys Glu Tyr Ser Gly Arg Val Leu Asn Ile
 65                  70                  75                  80

Phe Arg Lys Leu Tyr Gly Lys Glu Ile Tyr Ala Lys Val Glu Ser Trp
                 85                  90                  95

Ser Asn Phe Pro Lys Ser Thr Gly Leu Ala Ser Ser Ala Ala Gly Ile
                100                 105                 110

Ala Ala Leu Val Tyr Ala Thr Asn Glu Ala Leu Glu Leu Gly Leu Ser
            115                 120                 125

Gln Lys Glu Leu Ser Lys Ile Ala Arg Ile Gly Ser Gly Ser Ala Cys
        130                 135                 140

Arg Ser Thr Ala Gly Gly Phe Val Leu Trp Glu Lys Gly Glu Arg Asp
145                 150                 155                 160

Asp Gly Glu Asp Ser Tyr Cys Tyr Ser Leu Phe Pro Glu Asn His Trp
                165                 170                 175

Lys Glu Leu Val Asp Ile Ile Ala Ile Val Ser Glu Lys Ser Lys Lys
                180                 185                 190

Ile Ser Ser Arg Glu Gly Met Ile Ile Thr Ala Lys Thr Ser Asn Leu
            195                 200                 205

Met Lys Cys Arg Leu Lys Phe Ile Glu Glu Thr Leu Pro Lys Val Ile
        210                 215                 220

Lys Ser Ile Glu Glu Arg Asn Glu Lys Glu Phe Tyr Tyr Trp Leu Met
225                 230                 235                 240

Arg His Ser Asn Ser Met His Ala Val Ile Leu Asp Ser Trp Pro Ser
                245                 250                 255

Phe Phe Tyr Leu Asn Asp Thr Ser Leu Lys Ile Met Glu Trp Ile Gln
                260                 265                 270

Glu Phe Gly Lys Ala Gly Tyr Thr Phe Asp Ala Gly Pro Asn Pro His
            275                 280                 285

Ile Phe Thr Thr Glu Lys Tyr Lys Asp Glu Val Ile Arg Phe Leu Asn
        290                 295                 300

Ser Ile Gly Val Asn Lys Ile Ile Ile Ser Lys Val Gly Ser Gly Pro
305                 310                 315                 320

Lys Val Asn Lys Leu Leu
                325

<210> SEQ ID NO 19
<211> LENGTH: 317
<212> TYPE: PRT
<213> ORGANISM: Streptococcus pneumonia

<400> SEQUENCE: 19

Met Asp Arg Glu Pro Val Thr Val Arg Ser Tyr Ala Asn Ile Ala Ile
  1               5                  10                  15

Ile Lys Tyr Trp Gly Lys Lys Glu Lys Glu Met Val Pro Ala Thr
             20                  25                  30

Ser Ser Ile Ser Leu Thr Leu Glu Asn Met Tyr Thr Glu Thr Thr Leu
         35                  40                  45

Ser Pro Leu Pro Ala Asn Val Thr Ala Asp Glu Phe Tyr Ile Asn Gly
     50                  55                  60

Gln Leu Gln Asn Glu Val Glu His Ala Lys Met Ser Lys Ile Ile Asp
 65                  70                  75                  80

Arg Tyr Arg Pro Ala Gly Glu Gly Phe Val Arg Ile Asp Thr Gln Asn
```

```
                 85                  90                  95
Asn Met Pro Thr Ala Ala Gly Leu Ser Ser Ser Ser Gly Leu Ser
            100                 105                 110

Ala Leu Val Lys Ala Cys Asn Ala Tyr Phe Lys Leu Gly Leu Asp Arg
            115                 120                 125

Ser Gln Leu Ala Gln Glu Ala Lys Phe Ala Ser Gly Ser Ser Ser Arg
            130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
            165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
            195                 200                 205

Asp Tyr Gln Asp Met Leu Ile Tyr Leu Lys Glu Asn Asp Phe Ala Lys
            210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
            245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
            275                 280                 285

Asp Leu Glu His Leu Ser Glu Ile Phe Gly Gln Arg Tyr Arg Leu Ile
            290                 295                 300

Val Ser Lys Thr Lys Asp Leu Ser Gln Asp Cys Cys
305                 310                 315

<210> SEQ ID NO 20
<211> LENGTH: 389
<212> TYPE: PRT
<213> ORGANISM: Chloroflexus aggregans

<400> SEQUENCE: 20

Met Asn Glu Ser Ser Ile Pro Gln Gly Phe Ala Asp Leu Val Ala Pro
1               5                  10                  15

Met Arg Thr Ala His Glu Arg Ile Ile Ala Asp Leu Arg Arg His His
            20                  25                  30

Ile Glu Leu Pro Pro Pro His Leu Pro Ala Cys Arg Gln Gly
            35                  40                  45

Ile Ala Ala Ala Arg Ala Phe Pro Met Gln Gly Val Leu Lys Tyr His
            50                  55                  60

Gly Leu Ser Asp Trp Val Gln Arg Ile Ala Phe Leu Pro Ser Ile Ser
65                  70                  75                  80

Ile Asn Asn Ala Ala Ala His Thr Thr Thr Leu Val Glu Phe Asp Pro
            85                  90                  95

Ala Leu Pro Ala Asp Ser Ala Val Ile Gly Gly Val Pro Ala His Gly
            100                 105                 110

Arg Glu Leu Glu Arg Ile Val His Val Leu Asp Thr Val Arg Ser Leu
            115                 120                 125

Ala Gly Ile Thr Ser His Ala Arg Val Val Ser Arg Asn Ile Val Arg
            130                 135                 140
```

Thr Arg Thr Thr Gly Lys Gly Leu Gly Thr Ser Ala Ser Ala Ala Ala
145                 150                 155                 160

Ala Leu Ala Cys Ala Ala Val Gly Ala Ile Phe Gly Pro Glu Leu Ala
            165                 170                 175

Gly His Thr Arg Phe Leu Ser Thr Leu Ala Arg Arg Leu Ala Gly Ser
        180                 185                 190

Gly Cys Arg Ser Ala Ala Gly Gly Leu Ala Leu Trp Leu Ser Tyr Pro
    195                 200                 205

Gly Ile Pro Pro Asp Glu Ser Phe Ala Val Arg Leu Asp Gln Asp His
210                 215                 220

Glu Leu Asp Asp Leu Ala Leu Ile Thr Val Pro Ile Asp Ser Arg Ile
225                 230                 235                 240

Gly Leu Lys Thr Glu Gln Ala His His Asp Ala Pro Gln Ser Ile Phe
            245                 250                 255

Phe Arg Ala Trp Met Leu Ala Arg Gly Asp Glu Val Arg Glu Cys Ile
        260                 265                 270

Ala Ala Ala Arg Arg Gly Asp Trp Gln Thr Ile Gly Gln Leu Ala Glu
    275                 280                 285

Leu Asp Ser Met Arg Leu His Gly Val Thr Met Ser Gly Ser Arg Glu
290                 295                 300

Gln Lys Ile Ile Gly Trp Glu Pro Glu Asn Ile Thr Leu Phe Arg Leu
305                 310                 315                 320

Cys Asn Asp Leu Arg Ala Arg Gly Val Pro Val Tyr Ala Ser Thr Asp
            325                 330                 335

Thr Gly Pro Thr Val Val Phe Ile Thr Arg Arg Asp Phe Ala Pro Ile
        340                 345                 350

Val Thr Asp Ala Ile His His Ser Gly Leu Asn Val Glu Thr Val Ile
    355                 360                 365

Ala Pro Ile Gly Gly Pro Ala His Leu Ile Pro Val Glu Glu Ala Leu
370                 375                 380

Ala Glu Leu Gln Ser
385

<210> SEQ ID NO 21
<211> LENGTH: 324
<212> TYPE: PRT
<213> ORGANISM: Natronomonas pharaonis

<400> SEQUENCE: 21

Met Lys Ala Thr Ala Lys Ala His Pro Ile Gln Gly Leu Val Lys Tyr
1               5                   10                  15

His Gly Met Arg Asn Glu Glu Leu Arg Leu Pro Tyr His Asp Ser Ile
            20                  25                  30

Ser Val Cys Thr Ala Pro Ser His Ser Lys Thr Thr Ala Ala Phe Glu
        35                  40                  45

Pro Glu Arg Asp Ala Asp Arg Tyr Val Val Asp Gly Glu Val Val Asp
    50                  55                  60

Gly Arg Gly Ala Glu Arg Ile Arg Ala Val Val Asp His Val Arg Asp
65                  70                  75                  80

Val Ala Asp Ile Asp His Arg Val Arg Leu Glu Ser Glu Asn Asp Phe
                85                  90                  95

Pro Thr Asn Ile Gly Phe Gly Ser Ser Ser Gly Phe Ala Ala Ala
            100                 105                 110

Ala Val Ala Leu Val Glu Ala Ala Gly Leu Glu Leu Ser His Pro Glu
        115                 120                 125

```
Ile Ser Thr Val Ala Arg Arg Gly Ser Ser Ala Ala Arg Ala Val
130                 135                 140

Thr Gly Ala Phe Ser Gln Leu Tyr Thr Gly Leu Asp Asp Ala Asp Cys
145                 150                 155                 160

Tyr Ser Glu Arg Leu Asp Thr Asp Leu Glu Asp Asp Leu Arg Thr Val
                165                 170                 175

Ala Ala Glu Ile Pro Ala Phe Lys His Thr Glu Glu Ala His Lys Glu
            180                 185                 190

Ala Ala Asp Ser His Met Phe Glu Ala Arg Leu Ala His Ile His Glu
        195                 200                 205

Gln Ile Ala Thr Met Arg Asn Ala Leu Arg Glu Asn Asp Phe Asp Arg
210                 215                 220

Val Phe Glu Leu Ala Glu His Asp Ser Leu Ser Leu Ala Ala Thr Thr
225                 230                 235                 240

Met Thr Gly Pro Ala Gly Trp Val Tyr Trp Gln Pro Glu Thr Leu Ser
                245                 250                 255

Val Phe Glu Thr Val Arg Thr Leu Arg Glu Asp Asp Ile Pro Val
                260                 265                 270

Tyr Phe Ser Thr Asp Thr Gly Ala Ser Val Tyr Val Asn Thr Thr Ala
            275                 280                 285

Asp His Val Asp Arg Val Glu Asn Ala Ile Ala Ala Leu Gly Val Asp
        290                 295                 300

Thr Arg Val Trp Glu Val Gly Pro Ala Glu Val Leu Pro Glu Ser
305                 310                 315                 320

Glu Ser Leu Phe

<210> SEQ ID NO 22
<211> LENGTH: 396
<212> TYPE: PRT
<213> ORGANISM: Saccharomyces cerevisiae

<400> SEQUENCE: 22

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
                20                  25                  30

Ser Ser Ile Ser Val Thr Leu Ser Gln Asp Asp Leu Arg Thr Leu Thr
            35                  40                  45

Ser Ala Ala Thr Ala Pro Glu Phe Glu Arg Asp Thr Leu Trp Leu Asn
        50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175
```

```
                              -continued
Asp Ser Met Ala Val Gln Ile Ala Asp Ser Ser Asp Trp Pro Gln Met
            180                 185                 190
Lys Ala Cys Val Leu Val Val Ser Asp Ile Lys Lys Asp Val Ser Ser
        195                 200                 205
Thr Gln Gly Met Gln Leu Thr Val Ala Thr Ser Glu Leu Phe Lys Glu
    210                 215                 220
Arg Ile Glu His Val Val Pro Lys Arg Phe Glu Val Met Arg Lys Ala
225                 230                 235                 240
Ile Val Glu Lys Asp Phe Ala Thr Phe Ala Lys Glu Thr Met Met Asp
                245                 250                 255
Ser Asn Ser Phe His Ala Thr Cys Leu Asp Ser Phe Pro Pro Ile Phe
            260                 265                 270
Tyr Met Asn Asp Thr Ser Lys Arg Ile Ile Ser Trp Cys His Thr Ile
        275                 280                 285
Asn Gln Phe Tyr Gly Glu Thr Ile Val Ala Tyr Thr Phe Asp Ala Gly
    290                 295                 300
Pro Asn Ala Val Leu Tyr Tyr Leu Ala Glu Asn Glu Ser Lys Leu Phe
305                 310                 315                 320
Ala Phe Ile Tyr Lys Leu Phe Gly Ser Val Pro Gly Trp Asp Lys Lys
                325                 330                 335
Phe Thr Thr Glu Gln Leu Glu Ala Phe Asn His Gln Phe Glu Ser Ser
            340                 345                 350
Asn Phe Thr Ala Arg Glu Leu Asp Leu Glu Leu Gln Lys Asp Val Ala
        355                 360                 365
Arg Val Ile Leu Thr Gln Val Gly Ser Gly Pro Gln Glu Thr Asn Glu
    370                 375                 380
Ser Leu Ile Asp Ala Lys Thr Gly Leu Pro Lys Glu
385                 390                 395
```

METHOD FOR THE ENZYMATIC PRODUCTION OF ISOPRENOL USING MEVALONATE AS A SUBSTRATE

The present invention relates to a method for the production of isoprenol using mevalonate as a substrate and enzymatically converting it into isoprenol. Moreover, the present invention relates to a method for the production of isoprene comprising the method for the production of isoprenol using mevalonate as a substrate and enzymatically converting it by a decarboxylation step into isoprenol and further comprising the step of converting the produced isoprenol into isoprene.

The present invention also relates to a method for the production of isoamyl alcohol comprising the method for the production of isoprenol using mevalonate as a substrate and enzymatically converting it by a decarboxylation step into isoprenol and further comprising the step of converting the produced isoprenol into isoamyl alcohol.

Isoprenol responds to the formula $C_5H_{10}O$. It can be used to produce prenol which is used in perfumes or as a building block in the pharmaceutical industry, e.g. in the production of citral, vitamin A and vitamin E. It is chemically produced by the condensation of isobutene and formaldehyde, leading to isoprenol further isomerised into prenol.

The biological route which is presently used to produce isoprenol involves the mevalonate pathway: mevalonate is produced, then diphosphorylated, then decarboxylated-dehydrated into isoprenyl-pyrophosphate, and finally dephosphorylated twice into isoprenol (U.S. patent application 20080092829). Isoprenol can be converted into isoprene which is a key compound for the tire industry, and also has many applications in the adhesives. It is produced chemically using several routes:

Extractive distillation from oil (C5 stream)
Dehydrogenation of iso-amylene
Double dehydrogenation of isopentane
Reaction of isobutene and formaldehyde
Reaction of acetone and acetylene
Propylene dimerization WO 2009/076676 reports a metabolic pathway to isoprene. The pathway is based on the dephosphorylation-dehydration of downstream intermediates in the mevalonate pathway, i.e. isoprenyl-pyrophosphate or prenyl-pyrophosphate. This process has the drawback of requiring going through the whole mevalonate pathway: double phosphorylation of mevalonate, followed by a decarboxylation-dehydration into isoprenyl-pyrophosphate, further isomerised into prenyl-pyrophosphate, and finally double dephosphorylation/dehydration into isoprene.

Isoamyl alcohol is a very important chemical commonly used as solvents for fats, oils, resins and alkaloids. There is a demand for isoamyl alcohol in perfumery industry, for example in the manufacture of isoamyl salicylate used in soap and cosmetic fragrances. It is also used in the manufacture of phosphoric acid. Furthermore, it is used in the synthesis of pyrethroids. Commercial processes for the production of isoamyl alcohol include fractionation of fusel oils, chlorination of alkanes with subsequent hydrolysis to produce a mixture of isomers and a low pressure oxo-process or hydroformylation of n-butenes followed by hydrogenation of the resulting iso-valeraldehyde.

WO 2011/076261 describes a process for producing isoprenol by enzymatic conversion of mevalonate with an enzyme having the activity of a decarboxylase. Although the method described in WO 2011/076261 allows to produce isoprenol by enzymatically converting mevalonate, there is still a need for improvements, in particular as regards efficiency of the process so as to make it suitable for industrial purposes. The present application addresses this need.

Thus, in a first aspect, the present invention relates to a method for producing isoprenol from mevalonate. In particular, the present invention relates to a method for producing isoprenol from mevalonate through a biological process, in particular an enzymatic process, in which two types of enzymes are combined in order to increase the efficiency of the production rate. More specifically, the present invention relates to a method for producing isoprenol, characterized in that it comprises the conversion of mevalonate into isoprenol by (i) a first enzyme having an activity of converting mevalonate into mevalonate 3-phosphate; and
(ii) a second enzyme being different from the first enzyme and having an activity of converting said mevalonate 3-phosphate into isoprenol.

The present invention also relates to the use of at least two enzymes, wherein one enzyme is selected from (i) as specified above and the other enzyme is selected from (ii) as specified above or of a microorganism producing said combination of enzymes, for producing isoprenol from mevalonate.

The present invention also relates to organisms, preferably microorganisms, which produce at least two enzymes, wherein one enzyme is selected from (i) as specified above and the other enzyme is selected from (ii) as specified above.

The term "mevalonate" comprises mevalonic acid as well as the anion of mevalonic acid which is the predominant form in biological media. Mevalonic acid is a precursor in the biosynthetic pathway, known as the mevalonate pathway that produces terpenes and steroids. Mevalonate is the primary precursor of isoprenyl pyrophosphate that is in turn the basis for all terpenoids. The structural formula of mevalonic acid is shown in FIG. 1. Mevalonic acid (3,5-dihydroxy-5-methylpentanoic acid) is chiral and exists in two enantiomers, R and S. In the present invention the term "mevalonic acid" encompasses both chiral forms, even if one of the two forms, for example the R form, is the one mainly produced naturally.

In the context of the present invention the term isoprenol comprises compounds which respond to the formula $C_5H_{10}O$. The IUPAC name of isoprenol is 3-methylbut3-en-1-ol. Synonyms of isoprenol are, for example, 2-methyl-1-buten-4-ol, 3-buten-1-ol-3-methyl, 3-isopentenyl alcohol, 3-methyl-3-buten-1-ol, isobutenylcarbinol, isopropenyl-ethyl alcohol and methallyl carbinol.

Figure 2:
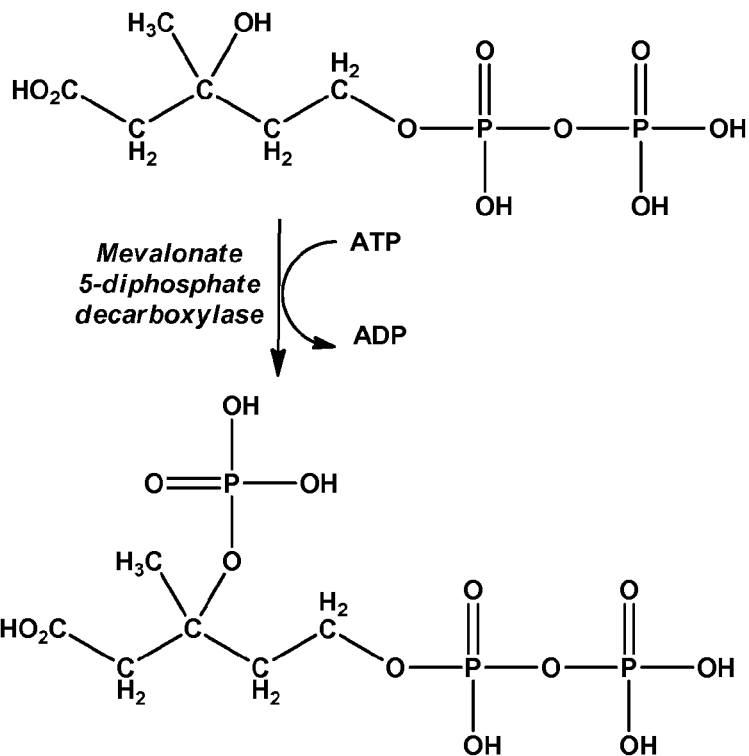
Figure 2:
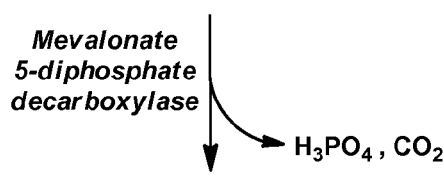
Figure 2:
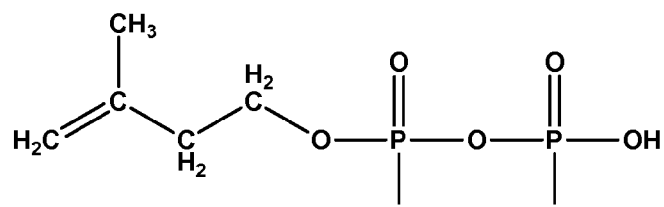
Figure 2:
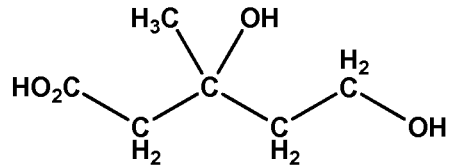
Figure 2:
Figure 2:
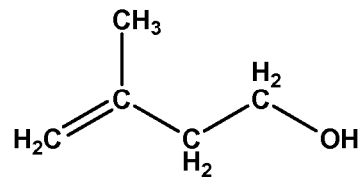

As mentioned above, WO 2011/076261 describes a process for producing isoprenol by enzymatic conversion of mevalonate with an enzyme having the activity of a decarboxylase. It has been described in WO 2011/076261 that generally the conversion of mevalonate into isoprenol by an enzyme having a decarboxylase activity, e.g. a mevalonate diphosphate (MDP) decarboxylase (E.C. 4.1.1.33), takes place by the conversion of mevalonate into mevalonate 3-phosphate which is then dephosphorylated/decarboxylated to lead to isoprenol. The generic reaction carried out by MDP decarboxylase using mevalonate diphosphate is depicted in FIG. 2. In the case of the natural reaction of mevalonate diphosphate decarboxylase with its natural substrate mevalonate 5-diphosphate, the first step of the reaction, i.e. the phosphorylation step, leads to an intermediate (3-phosphonoxy-3-methyl-5diphosphopentanoate; see FIG. 2A) which is unstable. The phosphorylation of mevalonate 5-diphosphate therefore facilitates the second step of the reaction, i.e. the concerted release of the phosphate (dephosphorylation) and of $CO_2$ (decarboxylation) to produce isopentenyl diphosphate (Byres et al., J. Mol. Biol. 371 (2007), 540-553). Since the two steps of the reaction are catalyzed by the same enzyme, it was assumed that when using mevalonate as a substrate the reaction would go through the same mechanism and would also involve an instable intermediate which is immediately converted by the enzyme via the second reaction step. This is also supported by Dhe-Paganon et al. (Biochemistry 1994, 33, 13355-13362) which describes experiments carried out with the yeast mevalonate diphosphate decarboxylase as regards its mechanism of action and the mechanism of inhibition by fluorinated compounds. The authors concluded that the $C_3$-hydroxyl of mevalonate diphosphate is phosphorylated by ATP, generating p-Mev-pp, which ionizes, leaving a carbocation on $C_3$ which is rapidly followed by decarboxylation. Thus, it was the understanding that the intermediate of the reaction catalyzed by mevalonate diphosphate decarboxylases is immediately converted by the enzyme into the final product.

However, it has surprisingly been found that when using mevalonate as a substrate the intermediate of the reaction, i.e. mevalonate 3-phosphate, is not unstable but transiently accumulates (see Example 3). In particular, it has been found that the intermediate is not immediately converted by the enzyme but is set free and is therefore available as a substrate for another enzyme converting it into the final product. Moreover, it has been found that different decarboxylases, in particular mevalonate diphosphate decarboxylases, catalyze the two above mentioned steps with different efficiencies, i.e. that some decarboxylases catalyze the first step with a higher efficiency than other decarboxylases and that some decarboxylases show a preference for the second step, i.e. the decarboxylation step. Due to this and the fact that the intermediate mevalonate 3-phosphate is not unstable and transiently accumulates it has now been found that it is possible to drastically increase the efficiency of the conversion of mevalonate into isoprenol as described in WO 2011/076261 by combining enzymes which show high catalytic activities for the first and the second step of the reaction, respectively. Thus, the present invention in particular relates to a method for achieving a higher efficiency in the enzymatic production of isoprenol from mevalonate, i.e. a method for improving the efficiency of such an enzymatic production.

The term "an enzyme having an activity of converting mevalonate into mevalonate 3-phosphate" means an enzyme which can phosphorylate mevalonate into mevalonate 3-phosphate. The phosphate group comes preferably from an ATP molecule.

This activity can, e.g., be measured as described in the attached Examples, in particular Example 2. One possibility is thus to incubate the respective enzyme with mevalonate and ATP and to measure the production of ADP (which reflects the production of mevalonate 3-phosphate). Assays for measuring the production of ADP are known to the person skilled in the art. One of these methods is the pyruvate kinase/lactate dehydrogenase assay described in Example 2. In this case the assay measures the rate of NADH absorbance decrease at 340 nm which is proportional to the ADP quantity. Alternatively, the activity can be measured by directly measuring the produced mevalonate 3-phosphate, e.g. by mass spectrometry. Such an assay is described in Example 3. In a preferred embodiment the term "an enzyme having an activity of converting mevalonate into mevalonate 3-phosphate" means an enzyme which can convert mevalonate and ATP into mevalonate 3-phosphate and ADP. Even more preferably such an enzyme can catalyze the reaction of converting mevalonate into mevalonate 3-phosphate, preferably the reaction of converting mevalonate and ATP into mevalonate 3-phosphate and ADP, with a $K_M$ of 10 mM or lower, e.g. with a $K_M$ of 5 mM or lower, preferably of 1 mM or lower and even more preferably of 0.1 mM or lower. In a particularly preferred embodiment such an enzyme can catalyze the reaction of converting mevalonate into mevalonate 3-phosphate, preferably the reaction of converting mevalonate and ATP into mevalonate 3-phosphate and ADP, with a $k_{cat}$ of at least 0.2 $s^{-1}$, preferably with a $k_{cat}$ of at least 0.5 $s^{-1}$, particularly preferred with a $k_{cat}$ of at least 1.0 $s^{-1}$, more preferred of at least 2.0 $s^{-1}$ and even more preferred with a $k_{cat}$ of at least 5.0 $s^{-1}$.

In a particularly preferred embodiment the capacity to convert mevalonate and ATP into mevalonate 3-phosphate and ADP is measured in an assay as described in Example 2 or as described in Example 3.

The term "an enzyme having an activity of converting said mevalonate 3-phosphate into isoprenol" means an enzyme which can catalyze a reaction by which there is a decarboxylation and dephosphorylation of the mevalonate 3-phosphate thereby leading to isoprenol.

This activity can, e.g., be measured as described in the appended Examples, in particular in Example 4 or 5. One possibility is thus to effect a combined enzyme assay in which the L200E mutant (SEQ ID NO: 16) of the Th. acidophilum mevalonate diphosphate decarboxylase is incubated with mevalonate and with the respective enzyme under conditions which allow the conversion of mevalonate into mevalonate 3-phosphate by the L200E mutant (SEQ ID NO: 16) of the Th. acidophilum mevalonate diphosphate decarboxylase and which in principle allow the decarboxylation and the dephosphorylation of mevalonate 3-phosphate into isoprenol and to detect the production of isoprenol, e.g. by gas chromatography. In a preferred embodiment such an assay is performed under the assay conditions described in Example 4 or 5. In a further preferred embodiment the term "an enzyme having an activity of converting mevalonate 3-phosphate into isoprenol" means an enzyme which is able to lead to an isoprenol production in such an assay which is at least half as high, more preferably at least as high as the isoprenol production which can be obtained by using in such an assay the L200E mutant (SEQ ID NO: 16) of the Th. acidophilum mevalonate diphosphate decarboxylase in combination with the mevalonate decarboxylase from S. mitis (SEQ ID NO: 10).

In a particularly preferred embodiment the capacity to produce isoprenol is measured in an assay as described in Example 4 or 5.

In one preferred embodiment an enzyme mentioned in (i) and (ii), above, is an enzyme which is considered by NCBI or an equivalent engine as having a COG3407 domain.

In a preferred embodiment of the method according to the invention the first enzyme (i) having an activity of converting mevalonate into mevalonate 3-phosphate is selected from the group consisting of (A) a protein comprising the amino acid sequence as shown in SEQ ID NO: 1 or a protein comprising an amino acid sequence which is at least 15% identical to the amino acid sequence shown in SEQ ID NO: 1 and showing an activity of converting mevalonate into mevalonate 3-phosphate which is at least as high as the corresponding activity of the protein having the amino acid sequence shown in SEQ ID NO: 1;

(B) a protein comprising the amino acid sequence as shown in SEQ ID NO: 2 or a protein comprising an amino acid sequence which is at least 15% identical to the amino acid sequence shown in SEQ ID NO: 2 and showing an activity of converting mevalonate into mevalonate 3-phosphate which is at least as high as the corresponding activity of the protein having the amino acid sequence shown in SEQ ID NO: 2;

(C) a protein comprising the amino acid sequence as shown in SEQ ID NO: 3 or a protein comprising an amino acid sequence which is at least 15% identical to the amino acid sequence shown in SEQ ID NO: 3 and showing an activity of converting mevalonate into mevalonate 3-phosphate which is at least as high as the corresponding activity of the protein having the amino acid sequence shown in SEQ ID NO: 3;

(D) a protein comprising the amino acid sequence as shown in SEQ ID NO: 4 or a protein comprising an amino acid sequence which is at least 15% identical to the amino acid sequence shown in SEQ ID NO: 4 and showing an activity of converting mevalonate into mevalonate 3-phosphate which is at least as high as the corresponding activity of the protein having the amino acid sequence shown in SEQ ID NO: 4; and (E) a protein comprising the amino acid sequence as shown in SEQ ID NO: 16 or a protein comprising an amino acid sequence which is at least 15% identical to the amino acid sequence shown in SEQ ID NO: 16 and showing an activity of converting mevalonate into mevalonate 3-phosphate which is at least as high as the corresponding activity of the protein having the amino acid sequence shown in SEQ ID NO: 16.

SEQ ID NO: 1 shows the amino acid sequence of an enzyme from *Picrophilus torridus* DSM 9790 (GenBank accession number AAT43941; Swissprot/TrEMBL accession number Q6KZB1).

SEQ ID NO: 2 shows the amino acid sequence of an enzyme from *Thermoplasma acidophilum* (GenBank accession number CAC12426; Swissprot/TrEMBL accession number Q9HIN1).

SEQ ID NO: 3 shows the amino acid sequence of an enzyme from *Thermoplasma volcanium* (GenBank accession number BAB59465; Swissprot/TrEMBL accession number Q97BY2).

SEQ ID NO: 4 shows the amino acid sequence of an enzyme from *Ferroplasma acidarmanus* fer1 (GenBank accession number ZP_05571615).

SEQ ID NO: 16 shows the amino acid sequence of the enzyme from *Thermoplasma acidophilum* (GenBank accession number CAC12426; Swissprot/TrEMBL accession number Q9HIN1) shown in SEQ ID NO: 2 in which the leucine (Leu) in position 200 is replaced by a glutamate (Glu).

In a further preferred embodiment of the method according to the invention the second enzyme (ii) having an activity of converting mevalonate 3-phosphate into isoprenol is selected from the group consisting of (a) a protein comprising the amino acid sequence as shown in SEQ ID NO: 5 or a protein comprising an amino acid sequence which is at least 15% identical to the amino acid sequence shown in SEQ ID NO: 5 and showing an activity of converting mevalonate 3-phosphate into isoprenol which is at least as high as the corresponding activity of the protein having the amino acid sequence shown in SEQ ID NO: 5;

(b) a protein comprising the amino acid sequence as shown in SEQ ID NO: 6 or a protein comprising an amino acid sequence which is at least 15% identical to the amino acid sequence shown in SEQ ID NO: 6 and showing an activity of converting mevalonate 3-phosphate into isoprenol which is at least as high as the corresponding activity of the protein having the amino acid sequence shown in SEQ ID NO: 6;

(c) a protein comprising the amino acid sequence as shown in SEQ ID NO: 7 or a protein comprising an amino acid sequence which is at least 15% identical to the amino acid sequence shown in SEQ ID NO: 7 and showing an activity of converting mevalonate 3-phosphate into isoprenol which is at least as high as the corresponding activity of the protein having the amino acid sequence shown in SEQ ID NO: 7;

(d) a protein comprising the amino acid sequence as shown in SEQ ID NO: 8 or a protein comprising an amino acid sequence which is at least 15% identical to the amino acid sequence shown in SEQ ID NO: 8 and showing an activity of converting mevalonate 3-phosphate into isoprenol which is at least as high as the corresponding activity of the protein having the amino acid sequence shown in SEQ ID NO: 8;

(e) a protein comprising the amino acid sequence as shown in SEQ ID NO: 9 or a protein comprising an amino acid sequence which is at least 15% identical to the amino acid sequence shown in SEQ ID NO: 9 and showing an activity of converting mevalonate 3-phosphate into isoprenol which is at least as high as the corresponding activity of the protein having the amino acid sequence shown in SEQ ID NO: 9;

(f) a protein comprising the amino acid sequence as shown in SEQ ID NO: 10 or a protein comprising an amino acid sequence which is at least 15% identical to the amino acid sequence shown in SEQ ID NO: 10 and showing an activity of converting mevalonate 3-phosphate into isoprenol which is at least as high as the corresponding activity of the protein having the amino acid sequence shown in SEQ ID NO: 10;

(g) a protein comprising the amino acid sequence as shown in SEQ ID NO: 11 or a protein comprising an amino acid sequence which is at least 15% identical to the amino acid sequence shown in SEQ ID NO: 11 and showing an activity of converting mevalonate 3-phosphate into isoprenol which is at least as high as the corresponding activity of the protein having the amino acid sequence shown in SEQ ID NO: 11;

(h) a protein comprising the amino acid sequence as shown in SEQ ID NO: 12 or a protein comprising an amino acid sequence which is at least 15% identical to the amino acid sequence shown in SEQ ID NO: 12 and showing an activity of converting mevalonate 3-phosphate into isoprenol which is at least as high as the corresponding activity of the protein having the amino acid sequence shown in SEQ ID NO: 12;

(i) a protein comprising the amino acid sequence as shown in SEQ ID NO: 13 or a protein comprising an amino acid sequence which is at least 15% identical to the amino acid sequence shown in SEQ ID NO: 13 and showing an activity of converting mevalonate 3-phosphate into isoprenol which is at least as high as the corresponding activity of the protein having the amino acid sequence shown in SEQ ID NO: 13;

(j) a protein comprising the amino acid sequence as shown in SEQ ID NO: 14 or a protein comprising an amino acid sequence which is at least 15% identical to the amino acid sequence shown in SEQ ID NO: 14 and showing an activity of converting mevalonate 3-phosphate into isoprenol which is at least as high as the corresponding activity of the protein having the amino acid sequence shown in SEQ ID NO: 14;

(k) a protein comprising the amino acid sequence as shown in SEQ ID NO: 15 or a protein comprising an amino acid sequence which is at least 15% identical to the amino acid sequence shown in SEQ ID NO: 15 and showing an activity of converting mevalonate 3-phosphate into isoprenol which is at least as high as the corresponding activity of the protein having the amino acid sequence shown in SEQ ID NO: 15;

(l) a protein comprising the amino acid sequence as shown in SEQ ID NO: 17 or a protein comprising an amino acid sequence which is at least 15% identical to the amino acid sequence shown in SEQ ID NO: 17 and showing an activity of converting mevalonate 3-phosphate into isoprenol which is at least as high as the corresponding activity of the protein having the amino acid sequence shown in SEQ ID NO: 17;

(m) a protein comprising the amino acid sequence as shown in SEQ ID NO: 18 or a protein comprising an amino acid sequence which is at least 15% identical to the amino acid sequence shown in SEQ ID NO: 18 and showing an activity of converting mevalonate 3-phosphate into isoprenol which is at least as high as the corresponding activity of the protein having the amino acid sequence shown in SEQ ID NO: 18;

(n) a protein comprising the amino acid sequence as shown in SEQ ID NO: 19 or a protein comprising an amino acid sequence which is at least 15% identical to the amino acid sequence shown in SEQ ID NO: 19 and showing an activity of converting mevalonate 3-phosphate into isoprenol which is at least as high as the corresponding activity of the protein having the amino acid sequence shown in SEQ ID NO: 19;

(o) a protein comprising the amino acid sequence as shown in SEQ ID NO: 20 or a protein comprising an amino acid sequence which is at least 15% identical to the amino acid sequence shown in SEQ ID NO: 20 and showing an activity of converting mevalonate 3-phosphate into isoprenol which is at least as high as the corresponding activity of the protein having the amino acid sequence shown in SEQ ID NO: 20;

(p) a protein comprising the amino acid sequence as shown in SEQ ID NO: 21 or a protein comprising an amino acid sequence which is at least 15% identical to the amino acid sequence shown in SEQ ID NO: 21 and showing an activity of converting mevalonate 3-phosphate into isoprenol which is at least as high as the corresponding activity of the protein having the amino acid sequence shown in SEQ ID NO: 21; and (q) a protein comprising the amino acid sequence as shown in SEQ ID NO: 22 or a protein comprising an amino acid sequence which is at least 15% identical to the amino acid sequence shown in SEQ ID NO: 22 and showing an activity of converting mevalonate 3-phosphate into isoprenol which is at least as high as the corresponding activity of the protein having the amino acid sequence shown in SEQ ID NO: 22.

SEQ ID NO: 5 shows the amino acid sequence of an enzyme cloned from *Streptococcus gordonii*. SEQ ID NO: 6 shows the amino acid sequence of an enzyme from *Streptococcus gordonii* str. Challis substr. CH1 (GenBank accession number AAT43941; Swissprot/TrEMBL accession number A8UU9). SEQ ID NO: 7 shows the amino acid sequence of an enzyme from *Streptococcus infantarius* subsp *infantarius* ATCC BAA-102 (GenBank accession number EDT48420.1; Swissprot/TrEMBL accession number B1SCG0). SEQ ID NO: 8 shows the amino acid sequence of *Dictyostelium discoideum* (GenBank accession number EAL68476.1; Swissprot/TrEMBL accession number Q54YQ9). SEQ ID NO: 9 shows the amino acid sequence of an enzyme from *Lactobacillus delbrueckii* (GenBank accession number CAI97800.1; Swissprot/TrEMBL accession number Q1GAB2). SEQ ID NO: 10 shows the amino acid sequence of an enzyme from *Streptococcus mitis* (strain B6) (GenBank accession number CBJ22986.1). SEQ ID NO: 11 shows the amino acid sequence of an enzyme from *Streptococcus gallolyticus* UCN34 (GenBank accession number CBI13757.1). SEQ ID NO: 12 shows the amino acid sequence of an enzyme from *Streptococcus sanguinis* SK36 (GenBank accession number ABN43791.1). SEQ ID NO: 13 shows the amino acid sequence of an enzyme from *Streptococcus* sp. M143 (GenBank accession number EFA24040.1). SEQ ID NO: 14 shows the amino acid sequence of an enzyme from *Streptococcus suis* 89/1591 (GenBank accession number EEF63672.1). SEQ ID NO: 15 shows the amino acid sequence of an enzyme from *Streptococcus salivarius* SK126 (GenBank accession number EEK09252).

SEQ ID NO: 17 shows the amino acid sequence of *Methanosarcina mazei* (GenBank accession number AAM31457.1; Swissprot/TrEMBL accession number Q8PW40).

SEQ ID NO: 18 shows the amino acid sequence of *Sulfolobus tokodaii* (GenBank accession number BAK54434.1; Swissprot/TrEMBL accession number F9VNS6).

SEQ ID NO: 19 shows the amino acid sequence of *Streptococcus pneumonia* (GenBank accession number EDT95457.1; Swissprot/TrEMBL accession number B2DRT0). SEQ ID NO: 20 shows the amino acid sequence of *Chloroflexus aggregans* (GenBank accession number ACL26234.1; Swissprot/TrEMBL accession number B8G8V9). SEQ ID NO: 21 shows the amino acid sequence *Natromonas pharaonis* (GenBank accession number CAI48881.1; Swissprot/TrEMBL accession number Q3ISK5). SEQ ID NO: 22 shows the amino acid sequence *Saccharomyces cerevisiae* (GenBank accession number CAA66158.1; Swissprot/TrEMBL accession number P32377).

In a preferred embodiment of the method according to the invention the first enzyme (i) is as defined in (E) above and the second enzyme (ii) is as defined in (a) or (b) mentioned above, even more preferably the second enzyme is as defined in (f), (n) or (q), mentioned above. As illustrated in the examples, the combination of these enzymes is particularly efficient at producing isoprenol compounds according to the present invention.

In another preferred embodiment of the method according to the invention the second enzyme (ii) having an activity of converting mevalonate 3-phosphate into isoprenol is selected from any one of the proteins listed in the following Table or from a protein comprising an amino acid sequence which is at least 15% identical to the amino acid sequence of such a protein and showing an activity of converting mevalonate 3-phosphate into isoprenol which is at least as high as the corresponding activity of said protein.

TABLE 1

| Organism | Ref sequence GenBank |
| --- | --- |
| *Methanosarcina mazei* | AAM31457.1 |
| *Methanocaldococcus jannaschii* | AAB98390.1 |

TABLE 1-continued

| Organism | Ref sequence GenBank |
|---|---|
| Staphylococcus saprophyticus | BAE19266.1 |
| Streptococcus agalactiae | EAO73731.1 |
| Enterococcus faecalis | AAO80711.1 |
| Flavobacterium johnsoniae | ABQ04421.1 |
| Bdellovibrio bacteriovorus | CAE79505.1 |
| Chloroflexus aurantiacus | A9WEU8.1 |
| Legionella pneumophila | CAH13175.1 |
| Listeria monocytogenes | EAL09343.1 |
| Metallosphaera sedula | ABP95731.1 |
| Staphylococcus epidermidis | AAO03959.1 |
| Streptococcus thermophilus | AAV60266.1 |
| Bacillus coagulans | EAY45229.1 |
| Chloroflexus aggregans | ACL26234.1 |
| Lactobacillus brevis | ABJ64001.1 |
| Lactobacillus fermentum | BAG27529.1 |
| Lactobacillus plantarum | CAD64155.1 |
| Lactobacillus salivarius | ABD99494.1 |
| Lactococcus lactis sp. lactis | AAK04503.1 |
| Dichelobacter nodosus | ABQ14154.1 |
| Flavobacterium psychrophilum | CAL42423.1 |
| Streptococcus pneumoniae | EDT95457.1 |
| Streptococcus pyogenes | AAT86835.1 |
| Streptococcus suis | ABP91444.1 |
| Staphylococcus haemolyticus | BAE05710.1 |
| Streptococcus equi | ACG62435.1 |
| Arabidopsis thaliana | AAC67348.1 |
| Borrelia afzelii | ABH01961.1 |
| Encephalitozoon cuniculi | CAD25409.1 |
| Streptomyces sp. | BAB07791.1 |
| Streptococcus agalactiae | EAO73731.1 |
| Streptococcus uberis | CAR41735.1 |
| Gallus gallus | XP_423130 |
| Salmo salmar | ACI34234 |

As mentioned above, not only the proteins having the specifically mentioned amino acid sequences listed in the respective SEQ ID NOs or in Table 1 can be used, but also proteins which are considered by NCBI or an equivalent engine as having a COG3407 domain and, more preferred, proteins the amino acid sequence of which shows a homology of at least 15% to the specifically mentioned amino acid sequence and which have a respective enzymatic activity at least as high as the activity of a protein having the specifically mentioned amino acid sequence. Preferred enzymes advantageously have at least x% homology, wherein x is selected from the group consisting of 20, 25, 20, 35, 40, 45, 50, 55 and 60. In a further preferred embodiment the enzyme has at least 65% sequence homology, preferably at least 70%, more preferably at least 75%, even more preferably, at least 80, 85, 90, 95, 96, 97, 98 or 99% homology to one of the sequences shown in SEQ ID NO: 1, 2, 3, 4, 5, 6, 7, 8, 9, 10, 11, 12, 13, 14, 15, 17, 18, 19, 20, 21 or 22 or to one of the sequences shown in Table 1. Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence.

The percent of sequence homology can be determined by different methods and by means of software programs known to one of skill in the art, such as for example the CLUSTAL method or BLAST and derived software, or by using a sequence comparison algorithm such as that described by Needleman and Wunsch (J. Mol. Biol., 1970, 48:443) or Smith and Waterman (J. Mol. Biol., 1981, 147: 195). When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences.

Preferably, the degree of identity is calculated over the complete length of the sequence. Moreover, if the term "homology" is used in the context of the present invention, this term preferably means "sequence identity".

Such proteins showing the indicated degree of homology can, e.g., be other enzymes which occur naturally or which have been prepared synthetically. They include in particular enzymes which can be selected for their ability to produce isoprenol according to the invention. Thus, a selection test comprises contacting the purified enzyme, or a microorganism producing the enzyme, with the substrate of the reaction and measuring the production of the respective compound, i.e. mevalonate 3-phosphate or isoprenol. Such tests are described in the experimental section. Such selection tests can also be used to screen for enzymes with an optimized enzymatic activity for the substrate, i.e. mevalonate, to be converted into mevalonate 3-phosphate or further into isoprenol, i.e. having an optimized activity with respect to mevalonate or mevalonate 3-phosphate.

Such methods are well-known in the art and include, e.g. protein engineering techniques such as random mutagenesis, massive mutagenesis, site-directed mutagenesis, DNA shuffling, synthetic shuffling, in vivo evolution, or complete synthesis of genes and subsequent screening for the desired enzymatic activity.

The enzyme used in the invention can thus be natural or synthetic, and produced by chemical, biological or genetic means. It can also be chemically modified, for example in order to improve its activity, resistance, specificity, purification, or to immobilize it on a support.

The combination of the enzymes as defined in (i) and (ii), hereinabove, is characterized in that it leads to a higher conversion rate of mevalonate into isoprenol, i.e. a higher production of isoprenol, than the conversion rate which would be achieved by either enzyme alone or the mere addition of the conversion rates which either enzyme achieves in isolation. Preferably, the conversion rate of the combination is at least 2 fold higher than the mere addition of the conversion rates achieved by the enzymes in isolation, more preferably at least 5-fold higher, even more preferably at least 8-fold higher, particularly preferred at least 10-fold higher and most preferred at least 15-fold higher.

It has been found that enzymes which are able to catalyze the above described reactions for converting mevalonate into isoprenol via mevalonate 3-phosphate are often enzymes which can be classified in the phylogenetic superfamily of mevalonate diphosphate (MDP) decarboxylases (enzyme nomenclature EC 4.1.1.33). MDP decarboxylase is an enzyme involved in cholesterol biosynthesis. Said enzyme has been isolated from a variety of organisms including animals, fungi, yeasts and some bacteria. It can also be expressed by some plants (Lalitha et al., Phytochemistry 24 (11), (1985), 2569-2571). Many genes encoding this enzyme have been cloned and sequenced. These enzymes are generally composed of 300 to 400 amino acids and use ATP as co-substrate, which is converted during the reaction to ADP and inorganic phosphate. The phosphate group is transferred from the ATP molecule to the tertiary alcohol of mevalonate diphosphate, releasing ADP. The reaction intermediate phosphorylated on the 3-hydroxyl group then undergoes elimination of the phosphate group, in the physiological case releasing isopentenyl diphosphate FIG. 2.

MDP decarboxylases belong to a large lass of metabolite kinases, the GHMP kinase superfamily. Analysis of data on structural features of MDP decarboxylases accessible from Uniprot reveal that they share a common structural motif references in InterPRO database as IPR020568 (from ebi.ac.uk/interpro/entry/IPR020568). Domain IPR020568 or ("domain 2 of the ribosomal protein S5") has a left-handed, 2-layer alpha/beta fold with a core structure consisting of beta(3)-alpha-beta-alpha. Domains with this fold are found in numerous kinases from the GHMP kinase family Accordingly, in a preferred embodiment, the enzyme defined in (i) or (ii) above, is a MDP decarboxylase. In the context of the present invention a MDP decarboxylase is defined as an enzyme which can at least catalyze the conversion of 5-diphospho-3-phosphomevalonate into isopentenyl-5-diphosphate and $CO_2$ or which can at least catalyze the reaction of converting mevalonate diphosphate and ATP into 5-diphospho-3-phosphomevalonate and ADP. Preferably, such an enzyme can catalyze both reactions.

In another preferred embodiment the enzyme defined in (i) above, is an enzyme as defined in (i) (B) or (E). The sequence shown in SEQ ID NO: 2 represents an enzyme identified in *Thermoplasma acidophilum*. SEQ ID NO: 16 is a mutant of SEQ ID NO: 2 in which the leucine (Leu) residue at position 200 is replaced by a glutamate (Glu) residue. In Genbank this enzyme is classified as a mevalonate diphosphate decarboxylase. However, it is known from Chen and Poulter (Biochemistry 49 (2010), 207-217) that in *Th. acidophilum* there exists an alternative mevalonate pathway which involves the action of a mevalonate-5-monophosphate decarboxylase. Thus, it is possible that the enzyme represented by SEQ ID NO: 2 actually represents a mevalonate-5-monophosphate decarboxylase.

The term "diphosphomevalonate decarboxylase" or "a protein/enzyme having the activity of a diphosphomevalonate decarboxylase" in the context of the present application also covers enzymes which are derived from a diphosphomevalonate decarboxylase, which are capable of catalyzing the decarboxylation of mevalonate but which only have a low affinity to their natural substrate, e.g. mevalonate diphosphate, or do no longer accept their natural substrate, e.g. mevalonate diphosphate. Such a modification of the preferred substrate allows to improve the conversion of mevalonate into isoprenol and to reduce the production of the possibly occurring by-product isoprenyl pyrophosphate. Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution", DNA shuffling or in vivo evolution.

For example, for genetic engineering in prokaryotic cells, a nucleic acid molecule encoding a diphosphomevalonate decarboxylase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used.

In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting diphosphomevalonate decarboxylase variants are then tested for their enzymatic activity and in particular for their capacity to prefer mevalonate as a substrate rather than mevalonate diphosphate.

Such methods for identifying variants with improved enzymatic properties as regards the production of isoprenol may also be carried out in the presence of a cofactor which allows for a steric and/or electronic complementation in the catalytic site of the enzyme due to the fact that the substrate mevalonate is shorter than the natural substrate mevalonate diphosphate. Examples for such a cofactor would be phosphono-phosphate or phosphonamido-phosphate (see FIG. 3) or orthophosphate.

The modified version of the diphosphomevalonate decarboxylase accepting or preferring mevalonate or mevalonate 3-phosphate as a substrate but having a low affinity to its natural product mevalonate diphosphate as a substrate or no longer accepting its natural product mevalonate diphosphate as a substrate may be derived from a naturally occurring diphosphomevalonate decarboxylase or from an already modified, optimized or synthetically synthesized diphosphomevalonate decarboxylase.

The enzymes employed in the process according to the present invention can be natural versions of the proteins or synthetic proteins as well as proteins which have been chemically synthesized or produced in a biological system or by recombinant processes. The enzymes may also be chemically modified, for example in order to improve their stability, resistance, e.g. to temperature, for facilitating their purification or their immobilization on a support. The enzymes may be used in isolated form, purified form, in immobilized form, as a crude or partially purified extract obtained from cells synthesizing the enzyme(s), as chemically synthesized enzymes, as recombinantly produced enzymes, in the form of organism/microorganisms producing them etc.

The method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising one or more cofactors). In one embodiment, the enzymes employed in the method are used in purified form.

For carrying out the process in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce isoprenol. The production of isoprenol can be measured by methods known in the art, such as chromatography, e.g. thin layer chromatography or liquid or gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In one embodiment, the conversion occurs in the presence of a co-substrate, said co-substrate preferably being a compound containing a phosphoanhydride, and preferably being ATP, an rNTP, a dNTP or a mixture of several of these molecules, a polyphosphate, or pyrophosphate. The co-substrate can be added to the reaction and is preferably selected from the group consisting of ATP, an rNTP, a dNTP, a mixture of several rNTPs or dNTPs, a polyphosphate, and preferably pyrophosphate, or a compound containing a phosphoanhydride (represented by the general formula X—PO$_3$H$_2$).

Although the decarboxylation step, i.e. the reaction defined as (ii) herein-above, does not require ATP consumption, it could be shown that the presence of ATP in the reaction could be beneficial. It is assumed that ATP might have an effect on the folding of the protein by the binding of ATP to the ATP-binding site of the diphosphomevalonate decarboxylase. In fact, this can be observed by eye: the purified enzyme has a tendency to precipitate, and the addition of ATP prevents this effect. It is considered that not only ATP but also other similar compounds like dATP, ADP, AMP or other NTPs or dNTPs have this effect. Thus, in a further embodiment, the method according to the present invention is carried with ATP, dATP, ADP, AMP or an NTP other than ATP or a dNTP as co-substrate.

In another embodiment, cofactors are added so as to best mimic the natural reaction or so as to provide steric or electronic complementation in the catalytic cleft. The structure of mevalonate leaves a space in the catalytic cleft empty during enzyme-substrate binding. Filling this space with a cofactor to replace the missing part of the substrate has the purpose of most closely mimicking the MDP molecule. As the cofactor is not modified during the reaction, it will therefore be added only in catalytic amounts. Examples for such a cofactor would be phosphono-phosphate or phosphonamido-phosphate (see FIG. 3) or orthophosphate.

Moreover, it is described for some diphosphomevalonate decarboxylase enzymes that they require monovalent and/or divalent cations. Thus, in a further embodiment, and if necessary, a suitable amount of a suitable monovalent (e.g. K$^+$) and/or divalent cation is added to the reaction when carrying out the method according to the invention. The divalent cation is preferably Mg$^{2+}$, Mn$^{2+}$ or Co$^{2+}$, but it is possible to also use other divalent cations such as Ca$^{2+}$. Of course, the nature of the monovalent and/or divalent cation depends on the need of the diphosphomevalonate decarboxylase enzyme in question.

In another embodiment the method according to the invention is carried out in culture, in the presence of an organism, preferably a microorganism, producing the enzymes. Thus, in such an embodiment of the invention, an organism, preferably a microorganism, that produces the enzymes specified in (i) and (ii) above is used. In a preferred embodiment, the (micro)organism is recombinant in that the enzymes specified in (i) and (ii) produced by the host are heterologous relative to the production host. The method can thus be carried out directly in the culture medium, without the need to separate or purify the enzymes. In an especially advantageous manner, a (micro)organism is used having the natural or artificial property of endogenously producing mevalonate, and also expressing or overexpressing the enzymes specified in (i) and (ii) above, natural or modified, so as to produce isoprenol directly from a carbon source present in solution.

In one embodiment the organism employed in the method according to the invention is an organism, preferably a microorganism, which has been genetically modified to contain a foreign nucleic acid molecule encoding an enzyme as defined above. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In a further embodiment the nucleic acid molecule is foreign to the organism/microorganism in that the encoded enzyme is not endogenous to the organism/microorganism, i.e. are naturally not expressed by the organism/microorganism when it is not genetically modified. In other words, the encoded enzyme is heterologous with respect to the organism/microorganism. The foreign nucleic acid molecule may be present in the organism/microorganism in extrachromosomal form, e.g. as plasmid, or stably integrated in the chromosome. A stable integration is preferred.

For example, the method according to the invention can be carried out by using microorganisms which produce mevalonate, for example an *E. coli* strain which naturally produce mevalonate or which have been genetically modified so as to produce (or overproduce) mevalonate] and which have been genetically engineered such that they overexpress the enzymes as defined in (i) and (ii) above, said enzymes preferably originating from an organism different from the host microorganism. The genetic modification can consist, e.g. in integrating the corresponding genes encoding the enzymes into the chromosome, expressing the enzymes from a plasmid containing a promoter upstream of the enzyme-coding sequence, the promoter and coding sequence preferably originating from different organisms, or any other method known to one of skill in the art.

Thus, for carrying out the process in vivo use is made of a suitable organism/microorganism(s) which is/are capable of providing mevalonate. There are two alternate pathways that lead to isoprenyl-pyrophosphate. One is the mevalonate pathway, observed in eukaryotes and some prokaryotes, especially in the firmicute phylum. All these organisms thus produce mevalonate. Most of the bacteria, including *E. coli*, use the other pathway (DXP pathway) and are thus not producing mevalonate. However, the latter can be genetically modified so as to produce mevalonate. For example, the implementation of the mevalonate pathway in *E. coli* has already been done successfully (Maury et al., FEBS Lett. 582 (2008), 4032). Overexpression of only the upstream part (thiolase, HMG-CoA synthase, HMG-CoA reductase) in organisms that have or that do not have the mevalonate pathway allows for the production of high levels of mevalonate.

The organisms used in the invention can be prokaryotes or eukaryotes, preferably, they are microorganisms such as bacteria, yeasts, fungi or molds, or plant cells or animal cells. In a particular embodiment, the microorganisms are bacteria, preferably of the genus *Escherichia* and even more preferably of the species *Escherichia coli*. In another embodiment, the microorganisms are recombinant bacteria of the genus *Escherichia*, preferably of the species *Escherichia coli*, having been modified so as to endogenously produce mevalonate and to convert it into isoprenol.

It is also possible to employ an extremophilic bacterium such as Thermus thermophilus, or anaerobic bacteria from the family Clostridiae.

In one embodiment the microorganism is a fungus, more preferably a fungus of the genus *Saccharomyces, Schizosaccharomyces, Aspergillus, Trichoderma, Pichia* or *Kluyveromyces* and even more preferably of the species *Saccharomyces cerevisiae, Schizosaccharomyces pombe, Aspergillus niger, Trichoderma reesei, Pichia pastoris* or of the species *Kluyveromyces lactis*. In a particularly preferred embodiment the microorganism is a recombinant yeast producing produce mevalonate and to convert it into isoprenol due to the expression of the enzymes specified in (i) and (ii) above.

In another preferred embodiment, the method according to the invention makes use of a photosynthetic microorganism expressing the enzymes as specified in (i) and (ii) above. Preferably, the microorganism is a photosynthetic bacterium, or a microalgae. In a further embodiment the microorganism is an algae, more preferably an algae belonging to the diatomeae.

Even more preferably such a microorganism has the natural or artificial property of endogenously producing mevalonate. In this case the microorganism would be capable of producing isoprenol directly from $CO_2$ present in solution.

It is also conceivable to use in the method according to the invention one microorganism that produces an enzyme as defined in (i) above and another microorganism which produces an enzyme as defined in (ii) above. Moreover, in a further embodiment at least one of the microorganisms is capable of producing mevalonate or, in an alternative embodiment, a further microorganism is used in the method which is capable of producing mevalonate.

In another embodiment the method according to the invention makes use of a multicellular organism expressing the enzymes as defined in (i) and (ii) above. Examples for such organisms are plants or animals.

In a particular embodiment, the method involves culturing microorganisms in standard culture conditions (30-37° C. at 1 atm, in a fermenter allowing aerobic growth of the bacteria) or non-standard conditions (higher temperature to correspond to the culture conditions of thermophilic organisms, for example).

When the process according to the invention is carried out in vivo by using an organism/microorganism providing the respective enzyme activities, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as eucalyptus, poplar or rubber tree (*Hevea brasiliensis*).

In another embodiment, the method according to the invention is characterized by the conversion of a carbon source such as glucose into mevalonate followed by the conversion of mevalonate into isoprenol.

In another embodiment, the method according to the invention comprises the production of isoprenol from atmospheric $CO_2$ or from $CO_2$ artificially added to the culture medium. In this case the method is implemented in an organism which is able to carry out photosynthesis, such as for example microalgae.

The present invention also relates to a method for producing isoprenol comprising the step of enzymatically converting mevalonate 3-phosphate into isoprenol by use of an enzyme which can catalyze the conversion via decarboxylation and dephosphorylation. As described above, the present application for the first time shows that the intermediate of the reaction leading from mevalonate to isoprenol is set free by the enzyme and can be used by another enzyme as a substrate. This opens up the possibility that the first and the second step of the reaction can be catalyzed by different enzymes thereby optimizing the overall reaction efficiency.

The method is preferably characterized in that the mevalonate 3-phosphate is provided as a substrate to the enzyme, i.e. is not produced by the enzyme itself from mevalonate but is taken up externally from the enzyme. Thus, the method is preferably characterized in that the mevalonate-3-phosphate is not produced in situ, wherein "in situ" means that the mevalonate-3-phosphate is not produced by the enzyme itself from mevalonate. Preferably, the mevalonate-3-phosphate is provided externally.

The present invention also relates to a composition comprising mevalonate-3-phosphate and an enzyme which can catalyze the conversion of mevalonate 3-phosphate into isoprenol via decarboxylation and dephosphorylation.

As regards the preferred enzyme to be used in such a method or composition, the same applies as has been set forth above in connection with (ii) of the method according to the invention as described herein-above.

Moreover, also with respect to the other preferred embodiments described above for the method according to the invention, the same applies to the method for producing isoprenol from mevalonate 3-phosphate.

Moreover, the present invention also relates to a composition comprising (a) mevalonate; and (b) a (micro)organism as described herein above. Such a composition may further comprise a suitable culture medium or a carbon source that can be converted into mevalonate.

The present invention also relates to a composition comprising
(a) mevalonate; and
(b) (i) a first enzyme having an activity of converting mevalonate into mevalonate 3-phosphate; and
(ii) a second enzyme being different from the first enzyme and having an activity of converting said mevalonate 3-phosphate into isoprenol.

For the preferred embodiments of the enzymes expressed by the (micro)organism and mentioned in (i) and (ii), above, the same applies as has already been set forth above in connection with the method according to the invention. In a particularly preferred embodiment, the composition also comprises a co-substrate (such as ATP), a co-factor and/or monovalent and/or divalent cations (such as $K^+$, $Mn^{2+}$, $Mg^{2+}$, $Co^{2+}$ or $Ca^{2+}$).

The present invention also relates to the use of a combination of at least two enzymes, wherein one enzyme is selected from the following (i) and the other enzyme is selected from the following (ii) or of an organism, preferably a microorganism, as described herein above or of a composition according to the invention, for producing isoprenol from mevalonate, wherein (i) and (ii) are as follows:
(i) a first enzyme having an activity of converting mevalonate into mevalonate 3-phosphate; and
(ii) a second enzyme being different from the first enzyme and having an activity of converting said mevalonate 3-phosphate into isoprenol.

As regards the preferred embodiments of the different components recited, the same applies as has been set forth above in connection with the method according to the invention.

In addition the present invention also relates to a method for producing isoprene from mevalonate comprising the method for producing isoprenol according to the invention as described above and further comprising the step of converting the produced isoprenol into isoprene. The conversion of isoprenol into isoprene can be achieved by means and methods known to the person skilled in the art. In particular, the respective reaction is a dehydration reaction.

Moreover, the present invention also relates to a method for producing isoamyl alcohol from mevalonate comprising the method for producing isoprenol according to the invention as described above and further comprising the step of converting the produced isoprenol into isoamyl alcohol. The conversion of isoprenol into isoamyl alcohol can be achieved by means and methods known to the person skilled in the art. In particular, the respective reaction is a hydrogenation reaction.

FIG. 1 Chemical structure of mevalonic acid.

FIG. 2 Reaction of diphosphomevalonate decarboxylase on the physiological substrate 5-diphosphomevalonate and on the precursor mevalonate.

Figure 3:
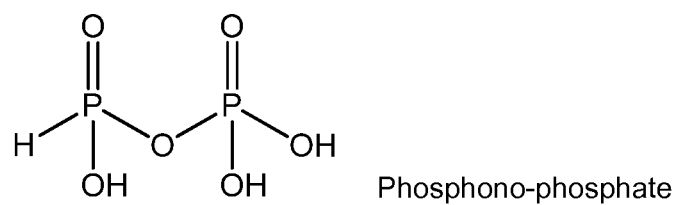
Figure 3:
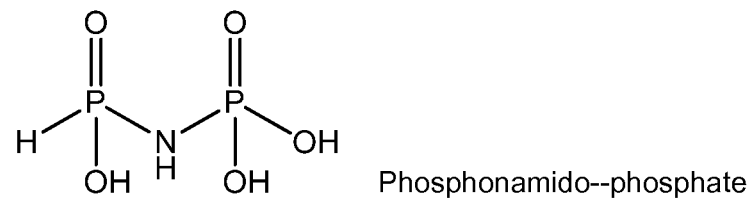

FIG. 3 Structure of phosphono-phosphate and phosphonoamido-phosphate

Figure 4:
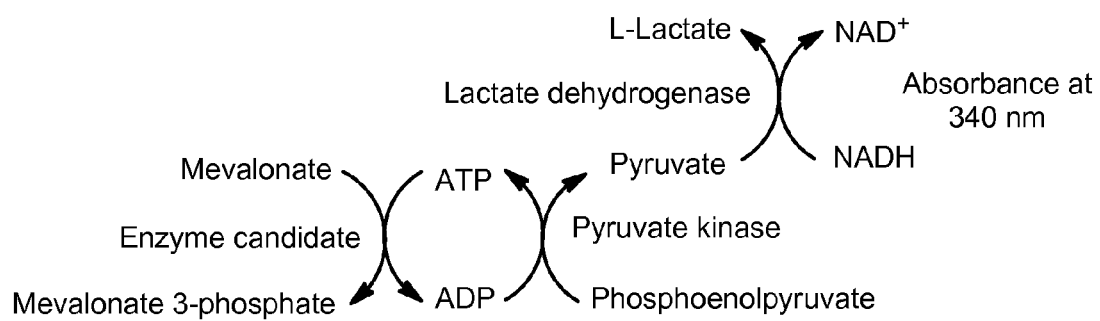

FIG. 4 Scheme of the ADP quantification assay, monitoring NADH consumption by the decrease of absorbance at 340 nm.

Figure 5:
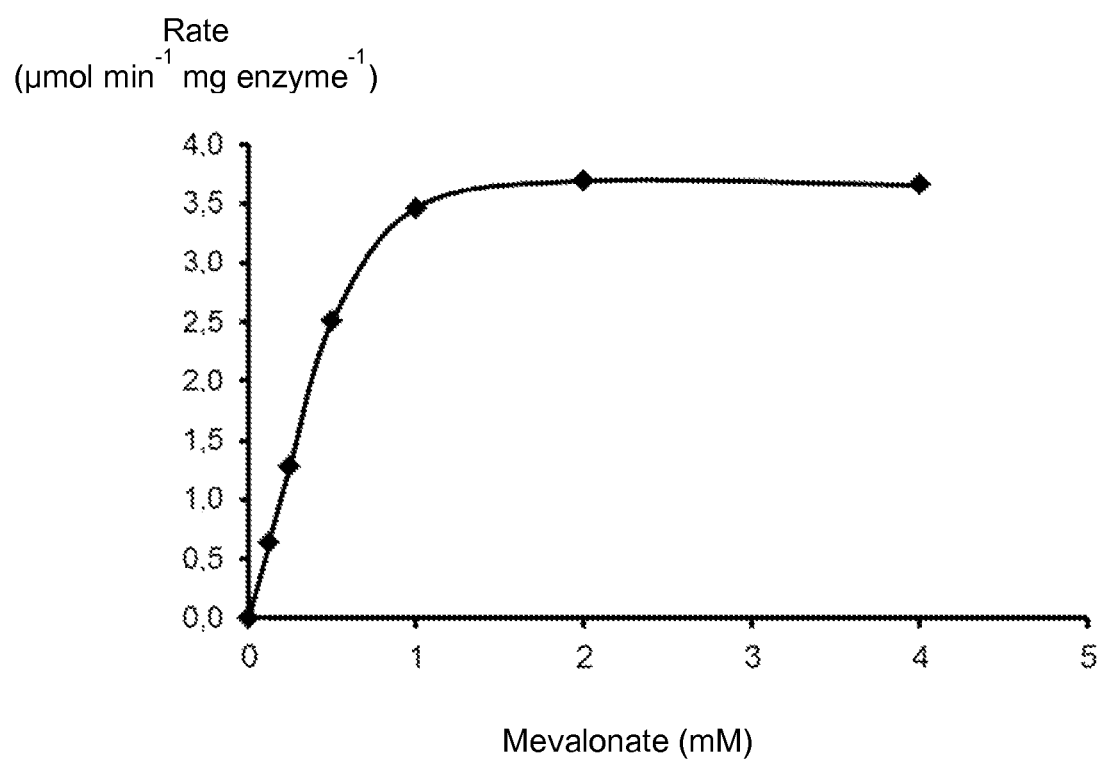

FIG. 5 Plot of the rate as a function of substrate concentration for the phosphotransferase reaction catalyzed by *Th. acidophilum* MDP decarboxylase (mutant L200E). Initial rates were computed from the kinetics over the 20 first minutes of the reaction.

Figure 6A:
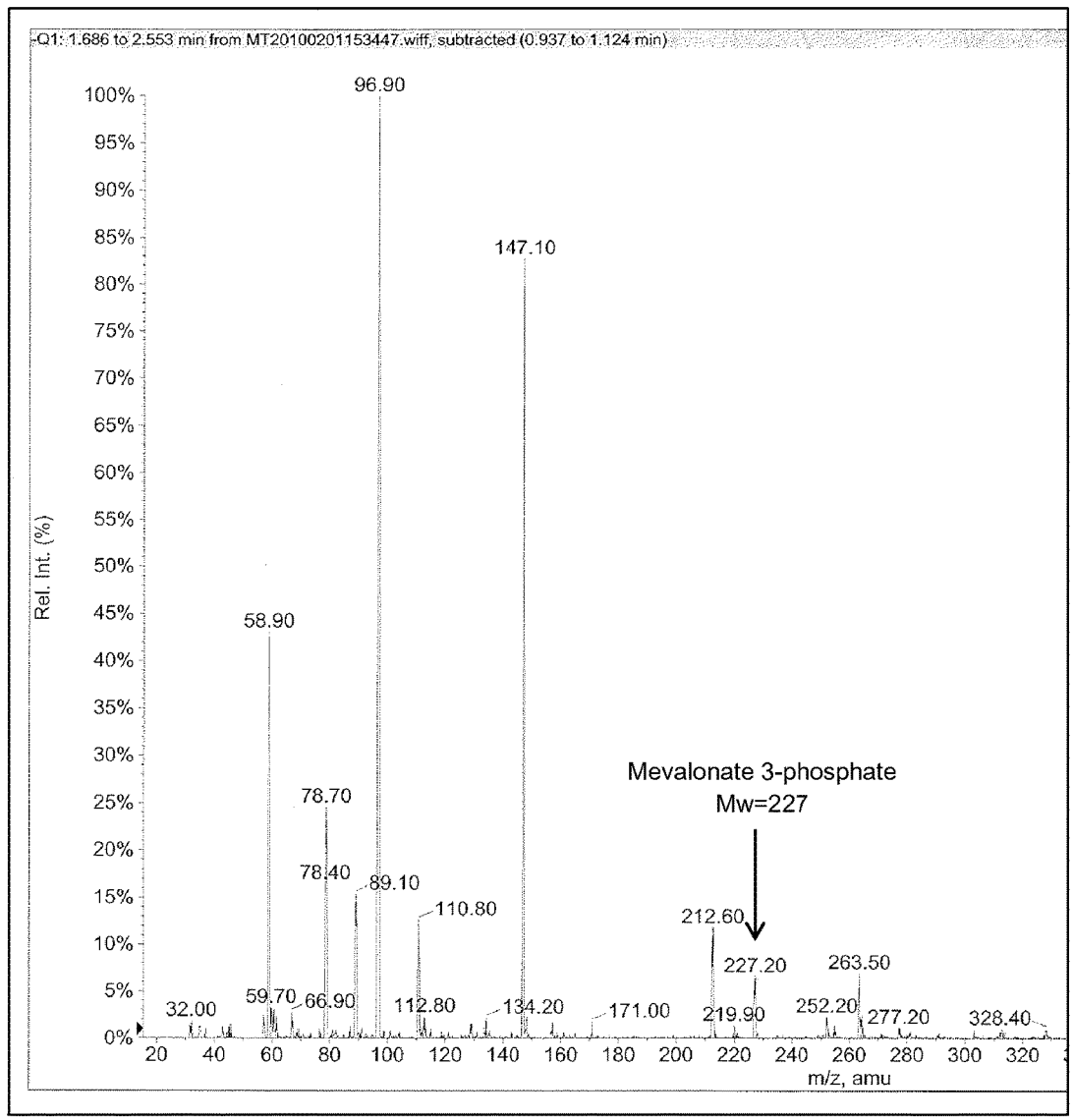

FIG. 6 Electrospray MS spectrums of mevalonate phosphorylation reaction catalyzed by MDP decarboxylase from *Th. acidophilum* (a), control assay without enzyme (b).

Figure 7:
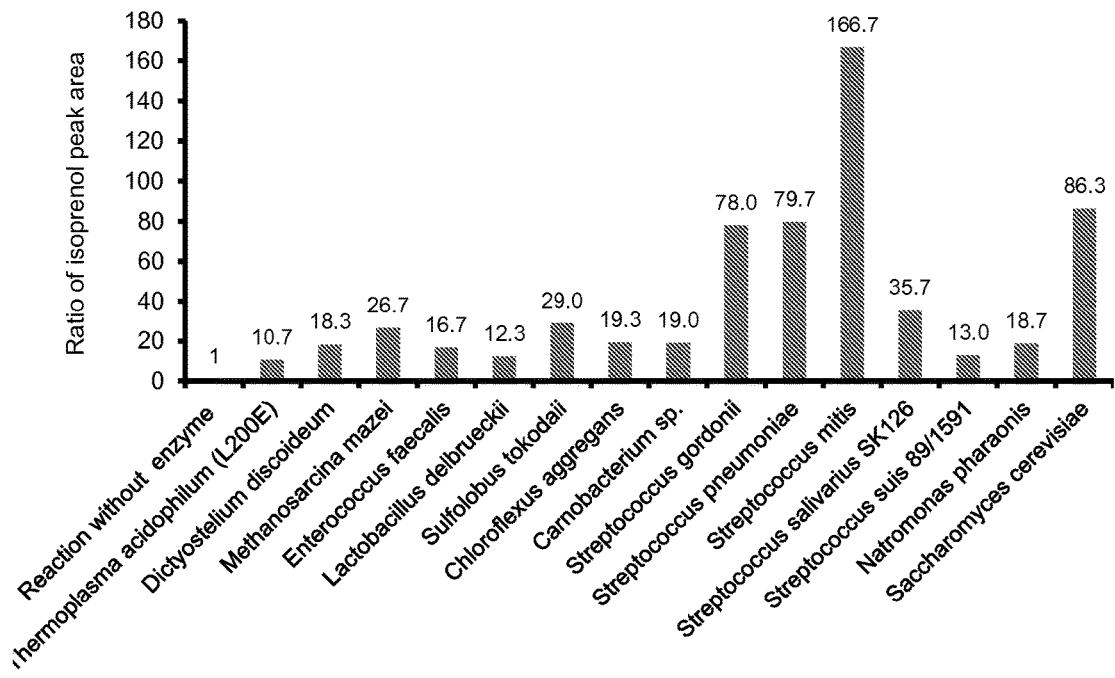

FIG. 7 Screening of MDP decarboxylases in a complementation assay. Peak area ratios were obtained by dividing the isoprenol peak area of each enzymatic assay by the peak area of the sample without enzyme (background noise).

Figure 8:
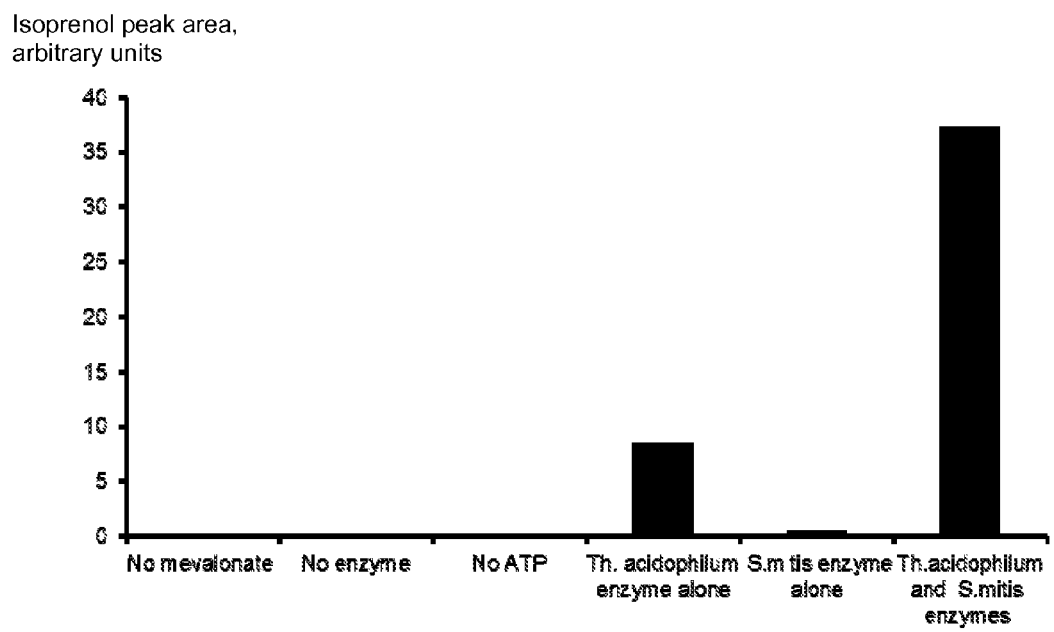

FIG. 8 Combined effect of MDP decarboxylase enzymes from *Th. acidophilum* and *S. mitis* for converting mevalonate into isoprenol.

FIG. 9 Mass spectrums of commercial isoprenol (a) and isoprenol produced from mevalonate by combining action of two enzymes (b). The characteristic ions 68 and 56 representing, respectively, the loss of H20 and CH2O were observed in both spectrums.

Figure 10:
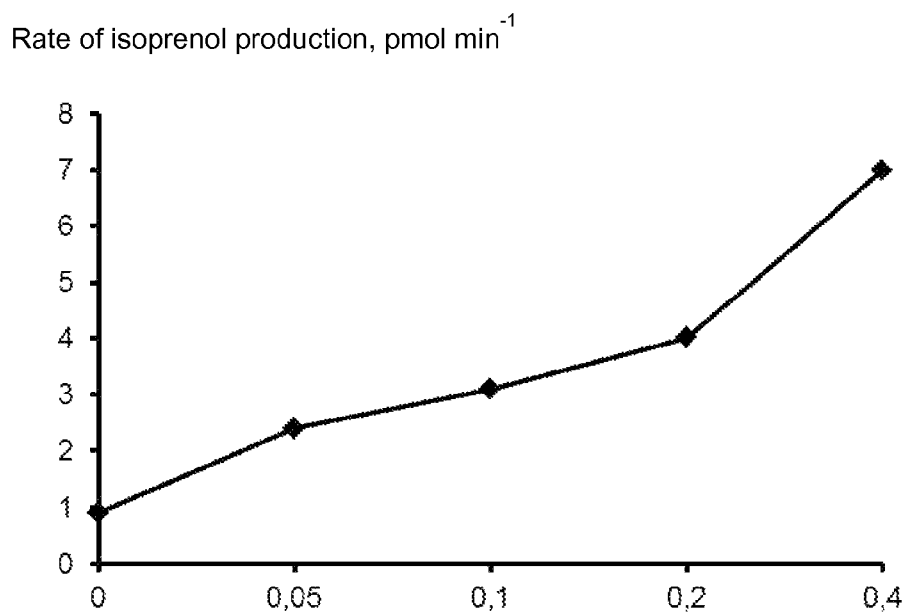

FIG. 10 Plot of the rate of isoprenol production as a function of the *S. gordonii* MDP decarboxylase concentration.

Figure 11:
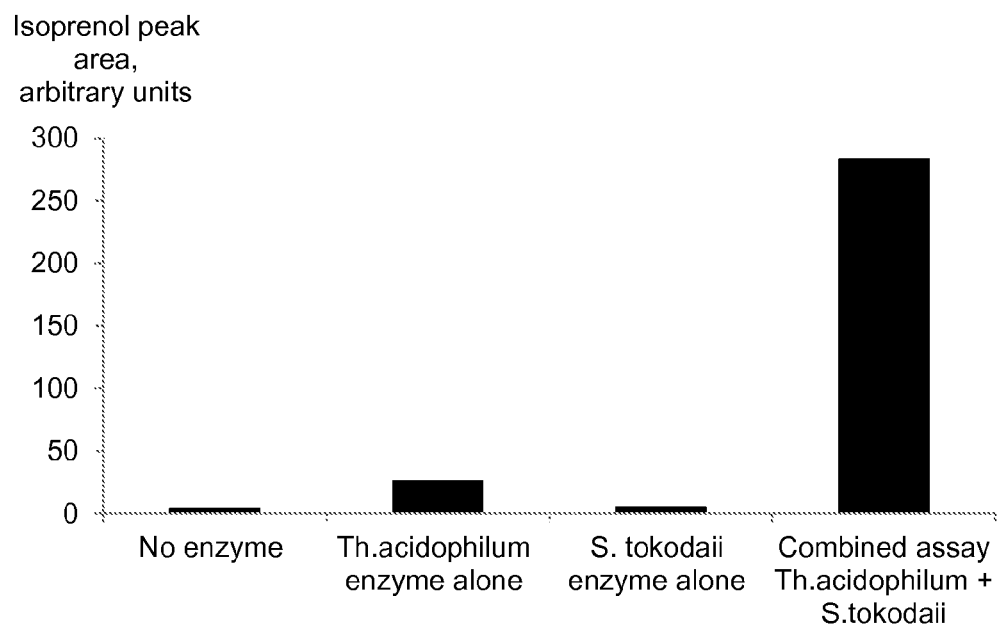

FIG. 11 Combined effect of MDP decarboxylase enzymes from *Th. acidophilum* and *S. tokodaii* for converting mevalonate into isoprenol.

Figure 12:
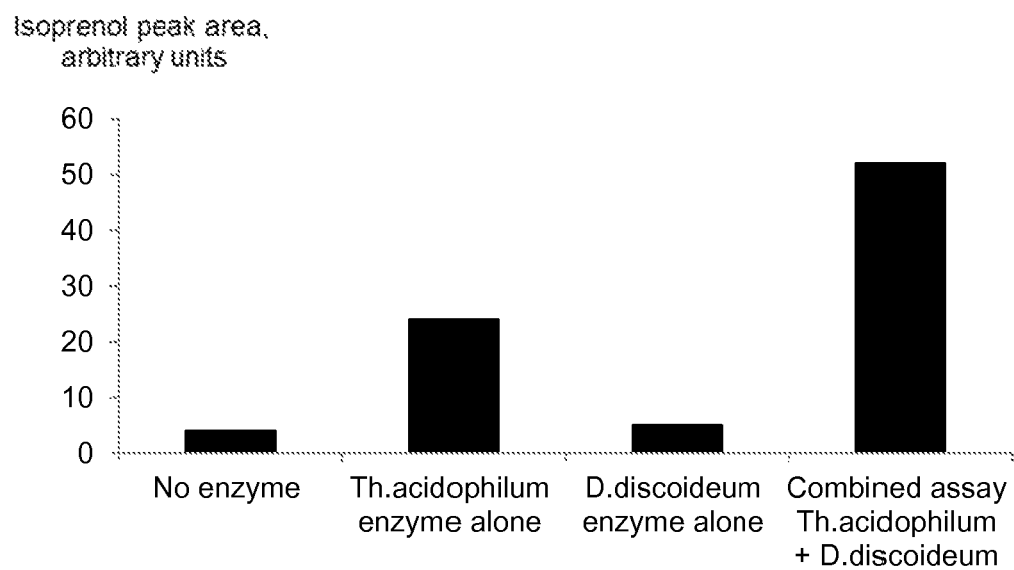

FIG. 12 Combined effect of MDP decarboxylase enzymes from *Th. acidophilum* and *D. discoideum* for converting mevalonate into isoprenol.

Other aspects and advantages of the invention will be described in the following examples, which are given for purposes of illustration and not by way of limitation

EXAMPLES

Example 1

Cloning, Expression and Purification of Enzymes

A set of genes encoding representatives of the diphosphomevalonate decarboxylase (MDP decarboxylase) family across eukaryotic, prokaryotic and archaeal organisms was constructed and tested to identify the most active candidates for improving isoprenol production.

Cloning, Bacterial Cultures and Expression of Proteins

The genes encoding mevalonate diphosphate (MDP) decarboxylase EC 4.1.1.33 were cloned in the pET 25b vector (Novagen) in the case of eukaryotic genes and in pET 22b (Novagen) in the case of prokaryotic genes. A stretch of 6 histidine codons was inserted after the methionine initiation codon to provide an affinity tag for purification. Competent *E. coli* BL21(DE3) cells (Novagen) were transformed with these vectors according to the heat shock procedure. The transformed cells were grown with shaking (160 rpm) on ZYM-5052 auto-induction medium (Studier F W, Prot. Exp. Pur. 41, (2005), 207-234) for 6 h at 37° C. and protein expression was continued at 28° C. overnight (approximately 16 h). The cells were collected by centrifugation at 4° C., 10,000 rpm for 20 min and the pellets were frozen at −80° C.

Protein Purification and Concentration

The pellets from 200 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) were added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-TED column (Macherey-Nagel) allowing adsorption of 6-His tagged proteins. Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 0.25 ml 50 mM Tris-HCl pH 7.5 containing 0.5 mM DTT and 5 mM $MgCl_2$. Protein concentrations were quantified by direct UV 280 nm measurement on the NanoDrop 1000 spectrophotometer (Thermo Scientific). The purity of proteins thus purified varied from 50% to 90%.

Example 2

Characterization of the Phosphotransferase Activity

The release of ADP that is associated with isoprenol production from mevalonate was quantified using the pyruvate kinase/lactate dehydrogenase coupled assay (FIG. 4). The MDP decarboxylases from *P. torridus* phylum and *S. mitis* enzyme were evaluated for their ability to phosphorylate mevalonate, releasing ADP.

The studied enzymatic reaction was carried out under the following conditions at 40° C.:
50 mM Tris-HCl pH 7.5
10 mM MgCl$_2$
100 mM KCl
5 mM ATP
0.4 mM NADH
1 mM Phosphoenolpyruvate
1.5 U/ml Lactate dehydrogenase
3 U/ml Pyruvate kinase
0 to 5 mM R,S-sodium Mevalonate
The pH was adjusted to 7.5.

Each assay was started by addition of particular enzyme (at a concentration from 0.025 to 1 mg/ml) and the disappearance of NADH was monitored by following the absorbance at 340 nm.

FIG. 5 shows an example of a Michaelis-Menten plot corresponding to the data collected for the *Th. acidophilum* (L200E) enzyme. The kinetic parameters are shown in the following Table 1.

TABLE 1

| Enzyme | $K_M$, mM | $k_{cat}$, s$^{-1}$ | $k_{cat}/K_M$, mM$^{-1}$s$^{-1}$ |
|---|---|---|---|
| *Ferroplasma acidarmanus* | 0.62 | 1.5 | 2.5 |
| *Picrophilus torridus* | 0.32 | 1.2 | 3.8 |
| *Thermoplasma volcanium* | 0.25 | 1.1 | 4.4 |
| *Thermoplasma acidophilum* | 0.32 | 1.5 | 4.7 |
| Mutant L200E of *Thermoplasma acidophilum* enzyme | 0.50 | 2.5 | 5.0 |
| *Streptococcus mitis* | 0.20 | 2 × 10$^{-3}$ | 0.01 |

Assays with MDP decarboxylases from the *P. torridus* phylum as well as *Streptococcus mitis* enzyme gave rise to a reproducible increase in ADP production in the presence of mevalonate. The enzymes from the *P. torridus* phylum displayed higher phosphotransferase activities than the *Streptococcus mitis* enzyme.

Example 3

Analysis of Mevalonate Phosphorylation by Mass Spectrometry

Figure 6B:
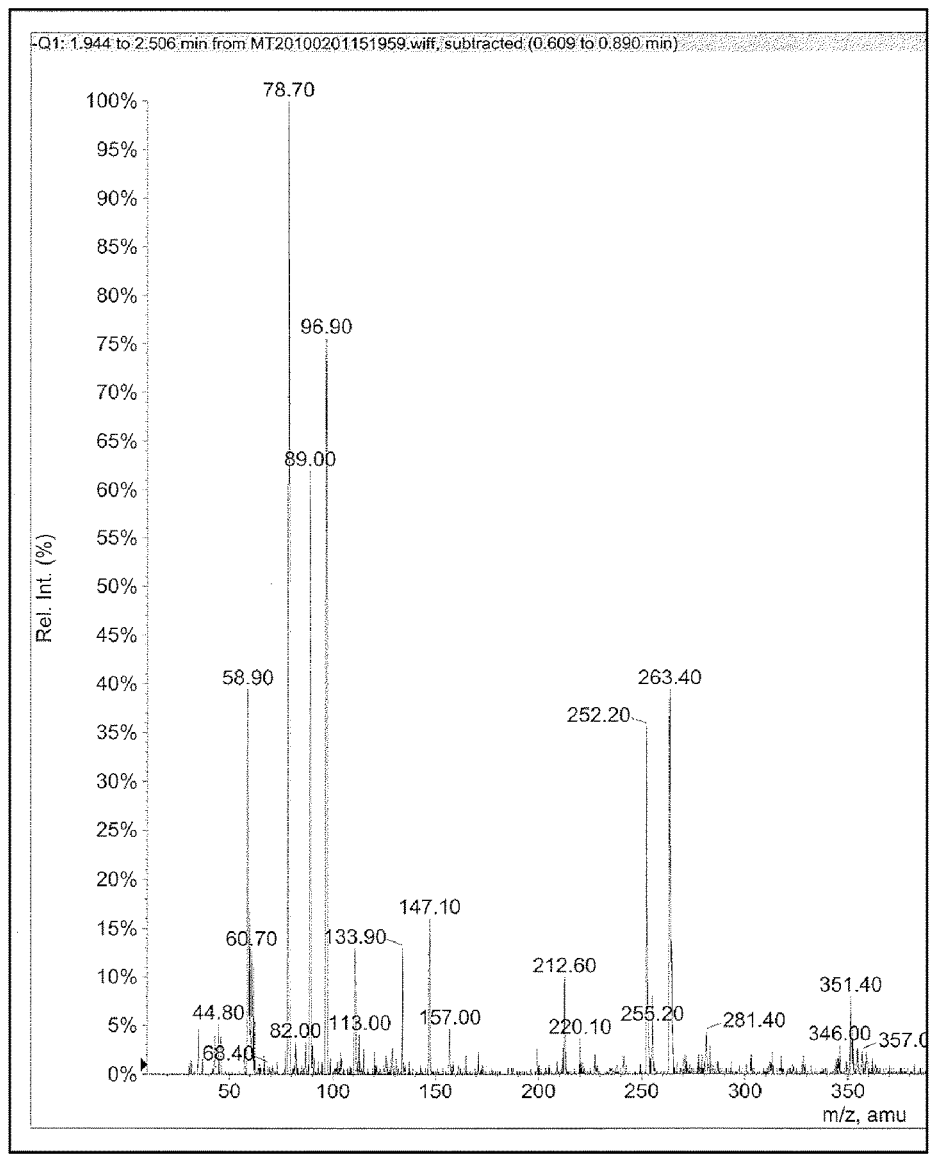

The mevalonate phosphorylation reactions were run under the following conditions:
50 mM Tris HCl pH 7.5
10 mM MgCl$_2$
20 mM KCl
40 mM ATP
200 mM R,S-sodium Mevalonate The assays were initiated by adding purified MDP decarboxylase (0.2 mg/ml) and incubated at 37° C. Control reactions were performed in which either no enzyme was added, or no substrate was added. Following incubation assays were processed by mass spectrometry analysis in negative ion mode. Typically, an aliquot of 80 µl reaction was removed, centrifuged and the supernatant was transferred to a clean vial. The product was then extracted with equal volume of ethyl acetate and diluted 1:5 (20%, vol/vol) with methanol. An aliquot of 10 µl was directly injected into mass spectrometer. Detection was performed by a PE SCIEX API 2000 quadrupole spectrometer interfaced to an electrospray ionisation (ESI) source. MS analysis showed an [M−H]$^-$ ion at m/z=227.20, corresponding to mevalonate 3-phosphate (3-phosphonoxy-3-methyl-5-hydroxypentanoate), from the complete enzymatic assay (FIG. 6a), but not from the control (FIG. 6b).

Example 4

Identification of Enzyme Combinations Leading to an Increased Isoprenol Production from Mevalonate MDP decarboxylases were evaluated using a complementation assay. *Th. acidophilum* MDP decarboxylase (mutant L200E) was incubated together with each tested enzyme from the library.

The combined enzymatic assay was carried out under the following conditions:
50 mM Tris HCl pH 7.5
10 mM MgCl$_2$
20 mM KCl
40 mM ATP
200 mM R,S-sodium Mevalonate
The pH was adjusted to 7.5

0.01 mg of the *Th. acidophilum* enzyme and 0.5 mg of the MDP decarboxylase to be tested were added to 0.1 ml of reaction mixture. Reaction mixture containing only 0.51 mg of the *Th. acidophilum* MDP decarboxylase (L200E) was used as reference. The assays were incubated without shaking at 37° C. for 24 h in a sealed vial (Interchim). The isoprenol production was analyzed as follows. An aliquot of 50 µl of liquid phase was removed and mixed with 100 µl of ethyl acetate. 100 µl of the upper ethyl acetate phase was transferred to a clean vial for analysis by gas chromatography. Commercial isoprenol was used as reference. The samples were analyzed on a Varian GC-430 gas chromatograph equipped with a flame ionization detector (FID). A 1 µl sample was separated on the DB-WAX column (30 m, 0.32×0.50 µm, Agilent) using the following gradient: 60° C. for 2 minutes, increasing the temperature at 20° C./minute to a temperature of 220° C. and hold at final temperature for 10 minutes. The retention time of isoprenol in these conditions was 7.38 min.

This screening procedure led to the identification of several archaeal, prokaryotic and eukaryotic MDP decarboxylases increasing the isoprenol production yield in combined assay (FIG. 7). The highest production of isoprenol was observed with enzymes from the *Streptococcus* genus, in particular with *S. mitis* MDP decarboxylase, and with the *S. cerevisiae* MDP decarboxylase.

Example 5

Detailed Study of Isoprenol Production from Mevalonate by Combining MDP Decarboxylase from *Th. Acidophilum* and MDP Decarboxylase from *S. Mitis*

The desired enzymatic reaction was carried out under the following conditions:
50 mM Tris HCl pH 7.5
10 mM MgCl$_2$
20 mM KCl
40 mM ATP
200 mM R,S-sodium Mevalonate 0.01 mg of purified MDP decarboxylase from *Th. acidophilum* (mutant L200E) and 0.2 mg of purified MDP decarboxylase from *S. mitis* were added to 0.1 ml of reaction mixture. Control reactions were performed in which either no enzyme was added, or no ATP was added.

To validate the combined action of two enzymes, a series of additional controls were carried out. In one assay, MDP decarboxylase from *S. mitis* (0.21 mg) was the only enzyme using as the catalyst. In the other experiment, 0.21 mg of the *Th. acidophilum* (L200E) enzyme was added, lacking *S. mitis* decarboxylase. The assays were incubated in a sealed vial (Interchim) without shaking for 24 hours at 37° C. Isoprenol extraction and analysis were performed according to the procedure described in Example 4.

The highest production of isoprenol was observed in the reaction mixture contained decarboxylase from *S. mitis* and decarboxylase from *Th. acidophilum* (FIG. 8). This indicated that the two enzymes present in the assay were performing complementarily the two steps of reaction producing isoprenol from mevalonate: transfer of the terminal phosphoryl group from ATP to the C3-oxygen of mevalonate followed by combined dephosphorylation-decarboxylation of the intermediate mevalonate 3-phosphate.

Figure 9A:
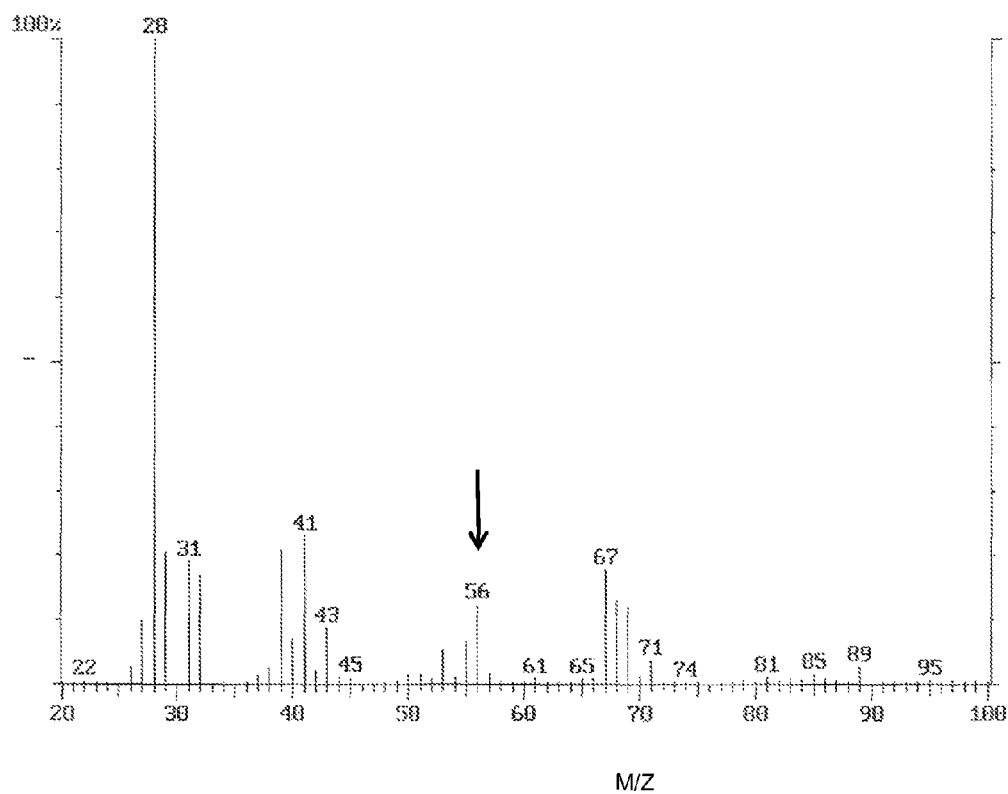
Figure 9B:
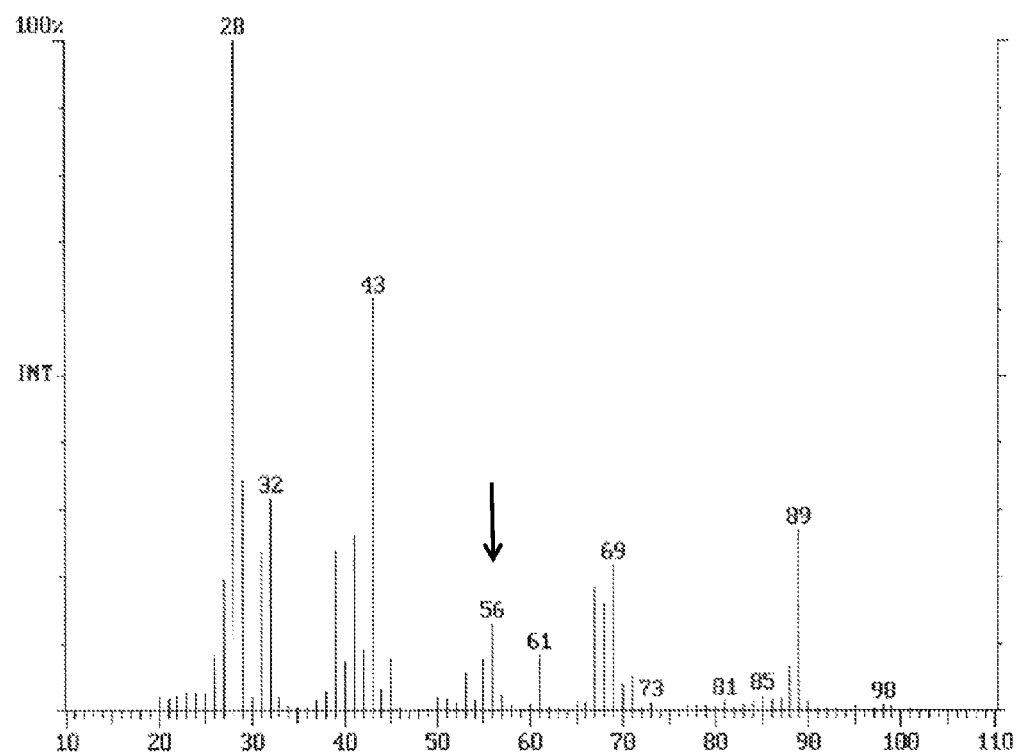

Gas chromatography-mass spectrometry (GC/MS) was then used to confirm the identity of the product detected by gas chromatography with flame ionization. The samples were analyzed on a Varian 3400Cx gas chromatograph equipped with Varian Saturn 3 mass selective detector. A mass spectrum of isoprenol obtained by enzymatic conversion of mevalonate was similar to this of commercial isoprenol (FIGS. 9a and 9b).

Example 6

Effect of Enzyme Concentration on Isoprenol Production Yield

The effect of *S. mitis* MDP decarboxylase concentration was assessed under the following conditions:
50 mM Tris HCl pH 7.5
10 mM $MgCl_2$
20 mM KCl
40 mM ATP
200 mM R,S-Mevalonate
0.01 mg of purified MDP decarboxylase from *Th. acidophilum* (mutant L200E) and a varying amount (from 0 to 0.4 mg) of purified MDP decarboxylase from *S. mitis* were added to 0.1 ml of reaction mixture. The mixtures were then incubated without shaking at 37° C. for 24 h in a sealed vial. Isoprenol extraction and analysis were performed according to the procedure described in Example 4. Increasing the *S. mitis* enzyme concentration resulted in an increase of the amount of produced isoprenol (FIG. 10).

Example 7

Detailed Study of Isoprenol Production from Mevalonate by Combining MDP Decarboxylase from *Th. Acidophilum* and MDP Decarboxylase from *S. Tokodaii*

The studied reaction was carried out under the following conditions:

50 mM Tris-HCl pH 7.5
10 mM $MgCl_2$
20 mM KCl
40 mM ATP
200 mM R,S-sodium mevalonate
0.01 mg of purified MDP decarboxylase from *Th. acidophilum* (L200E) and 0.4 mg MDP of decarboxylase from *S. tokodaii* were added to 0.1 ml of reaction mixture. A series of controls were performed in parallel under the same conditions. In one assay with MDP decarboxylase from *S. tokodaii* (0.41 mg) alone, containing no enzyme from *Th. acidophilum* was performed. In the other experiment, 0.41 mg of the *Th. acidophilum* (L200E) enzyme was added to the reaction mixture, lacking *S. tokodaii* decarboxylase.

The assays were incubated in sealed vials (Interchim) for 24 hours at 37° C. Isoprenol extraction was performed according to the procedure described in Example 4. Commercial isoprenol was used as reference.

Isoprenol production was then analyzed by gas-chromatography using Bruker 430-GC gas chromatograph equipped with flame ionization detector (FID) according to the following procedure:

5 µl of sample was separated on DB-WAX column (30 m, 0.32 mm×0.50 µm, Agilent Technologies) using the gradient described in Example 4.

The highest production of isoprenol was observed in the reaction mixture contained MDP decarboxylase *S. tokodaii* and MDP decarboxylase *Th. acidophilum* (FIG. 11). This indicates that the combination of two enzymes significantly increases isoprenol yield.

Example 8

Detailed Study of Isoprenol Production from Mevalonate by Combining MDP Decarboxylase from *Th. Acidophilum* and MDP Decarboxylase from *D. Discoideum*

The studied assay was carried out according the protocol described in Example 7.

0.01 mg of purified MDP decarboxylase from *Th. acidophilum* (L200E) and 0.4 mg MDP of decarboxylase from *D. discoideum* were added to 0.1 ml of reaction mixture. A series of control were performed in parallel under the same conditions. Assay with MDP decarboxylase from *D. discoideum* (0.41 mg) alone, containing no enzyme from *Th. acidophilum* was performed. In the other experiment, 0.41 mg of the *Th. acidophilum* (L200E) enzyme was added to the reaction mixture, lacking *D. discoideum* decarboxylase.

Isoprenol production was analyzed as described in Example 7.

The highest production of isoprenol was observed in the reaction mixture contained MDP decarboxylase *D. discoideum* and MDP decarboxylase *Th. acidophilum* (FIG. 12). Thus, higher isoprenol yield can be achieved by combining action of two enzymes on mevalonate.

The invention claimed is:

1. A multicellular organism or a microorganism comprising:
   (i) a first heterologous enzyme comprising an amino acid sequence at least 80% identical to the amino acid sequence shown in SEQ ID NO: 16 wherein said first heterologous enzyme converts mevalonate into mevalonate 3-phosphate; and
   (ii) a second heterologous enzyme being different from the first enzyme and comprising an amino acid sequence at least 80% identical to the amino acid sequence shown in SEQ ID NO: 10 wherein said second heterologous enzyme converts said mevalonate 3-phosphate into isoprenol,
   wherein the multicellular organism is a fungus, yeast, microalgae or plant,
   wherein the multicellular organism or microorganism is genetically modified to overproduce mevalonate and wherein the production of isoprenol by use of the combination of the first and second enzyme is higher than the production of isoprenol achieved by either enzyme alone or the addition of the production which either enzyme achieves in isolation.

2. The multicellular organism or a microorganism of claim 1, wherein
   (i) the first heterologous enzyme is selected from:
      (A) a protein comprising the amino acid sequence as shown in SEQ ID NO: 2; and
      (B) a protein comprising the amino acid sequence as shown in SEQ ID NO: 16.

3. The multicellular organism or a microorganism of claim 1, wherein
   (ii) the second heterologous enzyme is selected from:
      (A) a protein comprising the amino acid sequence as shown in SEQ ID NO: 10;
      (B) a protein comprising the amino acid sequence as shown in SEQ ID NO: 13; and
      (C) a protein comprising the amino acid sequence as shown in SEQ ID NO: 19.

4. The multicellular organism or a microorganism of claim 1 wherein
   (i) the first heterologous enzyme is selected from:
      (A) a protein comprising the amino acid sequence as shown in SEQ ID NO: 2; and
      (B) a protein comprising the amino acid sequence as shown in SEQ ID NO: 16; and
   (ii) the second heterologous enzyme is selected from:
      (A) a protein comprising the amino acid sequence as shown in SEQ ID NO: 10;
      (B) a protein comprising the amino acid sequence as shown in SEQ ID NO: 13; and
      (C) a protein comprising the amino acid sequence as shown in SEQ ID NO: 19.

5. A composition comprising the multicellular organism or a microorganism of claim 1.

6. A method of producing isoprenol comprising:
(i) culturing the multicellular organism or microorganism of claim 1 for a sufficient period of time to allow for the conversion of the mevalonate to isoprenol and
(ii) recovering said isoprenol.

7. A composition comprising the multicellular organism or a microorganism of claim 2.

8. The method of claim 6 wherein the first heterologous enzyme is selected from:
(A) a protein comprising the amino acid sequence as shown in SEQ ID NO: 2; and
(B) a protein comprising the amino acid sequence as shown in SEQ ID NO: 16.

9. A composition comprising the multicellular organism or a microorganism of claim 3.

10. The method of claim 6 wherein the second heterologous enzyme is selected from:
(A) a protein comprising the amino acid sequence as shown in SEQ ID NO: 10;
(B) a protein comprising the amino acid sequence as shown in SEQ ID NO: 13; and
(C) a protein comprising the amino acid sequence as shown in SEQ ID NO: 19.

11. A composition comprising the multicellular organism or a microorganism of claim 4.

12. The method of claim 6 wherein the first heterologous enzyme is selected from:
(A) a protein comprising the amino acid sequence as shown in SEQ ID NO: 2; and
(B) a protein comprising the amino acid sequence as shown in SEQ ID NO: 16; and
wherein said second heterologous enzyme is selected from:
(A) a protein comprising the amino acid sequence as shown in SEQ ID NO: 10;
(B) a protein comprising the amino acid sequence as shown in SEQ ID NO: 13; and
(C) a protein comprising the amino acid sequence as shown in SEQ ID NO: 19.

13. The method of claim 6, wherein the method further comprises:
(i) providing a composition comprising the first enzyme, the second enzyme and mevalonate; and
(ii) recovering said isoprenol.

14. The method of claim 6 wherein the method is carried out with ATP, dATP, ADP, AMP, an NTP other than ATP, a dNTP or pyrophosphate as co-substrate.

15. The method of claim 6, further comprising the step of converting isoprenol into isoprene.

16. The method of claim 6, further comprising the step of converting isoprenol into isoamyl alcohol.

17. The multicellular organism or the microorganism of claim 1, wherein the multicellular organism or the microorganism is genetically modified to comprise the genes encoding the mevalonate pathway.

18. The multicellular organism or the microorganism of claim 1, wherein the multicellular organism or the microorganism is genetically modified to comprise the genes encoding thiolase, HMG-CoA synthase, and HMG-CoA reductase.

19. The method of claim 6, wherein the multicellular organism or the microorganism is genetically modified to comprise the genes encoding the mevalonate pathway.

20. The method of claim 6, wherein the multicellular organism or the microorganism is genetically modified to comprise the genes encoding thiolase, HMG-CoA synthase, and HMG-CoA reductase.

* * * * *